(12) United States Patent
Cheng et al.

(10) Patent No.: US 10,973,429 B2
(45) Date of Patent: Apr. 13, 2021

(54) PRECISE LOCALIZATION OF CARDIAC ARRHYTHMIA USING INTERNAL ELECTROCARDIOGRAPH (ECG) SIGNALS SENSED AND STORED BY IMPLANTABLE DEVICE

(71) Applicant: Chelak iECG, Inc., Bellaire, TX (US)

(72) Inventors: Jie Cheng, Houston, TX (US); Dhanunjaya Lakkireddy, Leawood, KS (US)

(73) Assignee: Chelak iECG, Inc., Bellaire, TX (US)

( * ) Notice: Subject to any disclaimer, the term of this patent is extended or adjusted under 35 U.S.C. 154(b) by 27 days.

(21) Appl. No.: 16/255,571

(22) Filed: Jan. 23, 2019

(65) Prior Publication Data

US 2019/0223744 A1 Jul. 25, 2019

Related U.S. Application Data

(60) Provisional application No. 62/620,589, filed on Jan. 23, 2018.

(51) Int. Cl.
*A61B 5/00* (2006.01)
*A61B 5/0468* (2006.01)
(Continued)

(52) U.S. Cl.
CPC .......... *A61B 5/0468* (2013.01); *A61B 5/0036* (2018.08); *A61B 5/0044* (2013.01);
(Continued)

(58) Field of Classification Search
CPC ... A61B 5/0468; A61B 5/0432; A61B 5/0422; A61B 5/0464; A61B 5/686;
(Continued)

(56) References Cited

U.S. PATENT DOCUMENTS 4,387,717 A 6/1983 Brownlee et al.
4,750,494 A 6/1988 King
(Continued)

FOREIGN PATENT DOCUMENTS

WO 2000015294 A1 3/2000

OTHER PUBLICATIONS

International Search Report and Written Opinion dated Apr. 4, 2019, corresponding to Application No. PCT/US2019/014793.

*Primary Examiner* — Scott M. Getzow
(74) *Attorney, Agent, or Firm* — Cooley LLP

(57) ABSTRACT

Certain aspects of the present disclosure provide methods and apparatus for determining a precise localization of an arrhythmia origin or exit site in a heart of a subject using internal electrocardiograph (ECG) signals sensed and stored by an implantable device implanted in the subject. One example method of analyzing an arrhythmia in a subject generally includes reading, from an implantable device implanted in the subject, a plurality of internal ECG signals sensed and stored by the implantable device while the subject was experiencing an arrhythmia event (e.g., at any time, including while the subject was ambulatory); performing an analysis of the read internal ECG signals; and determining a localization of the arrhythmia associated with the arrhythmia event, based on the analysis.

23 Claims, 13 Drawing Sheets

(51) Int. Cl.
*A61N 1/362* (2006.01)
*A61B 5/0538* (2021.01)
*A61B 5/055* (2006.01)
*A61B 6/03* (2006.01)
*A61B 5/04* (2006.01)
*A61N 1/39* (2006.01)
*A61B 18/14* (2006.01)
*A61B 5/042* (2006.01)
*A61B 5/0432* (2006.01)
*A61B 5/0464* (2006.01)
*A61B 5/046* (2006.01)
*A61B 18/00* (2006.01)
*A61N 1/372* (2006.01)

(52) U.S. Cl.
CPC ............. *A61B 5/042* (2013.01); *A61B 5/046* (2013.01); *A61B 5/04011* (2013.01); *A61B 5/0422* (2013.01); *A61B 5/0432* (2013.01); *A61B 5/0464* (2013.01); *A61B 5/055* (2013.01); *A61B 5/0538* (2013.01); *A61B 5/686* (2013.01); *A61B 5/6869* (2013.01); *A61B 5/7235* (2013.01); *A61B 5/7239* (2013.01); *A61B 6/032* (2013.01); *A61B 6/037* (2013.01); *A61B 18/1492* (2013.01); *A61N 1/362* (2013.01); *A61N 1/3956* (2013.01); *A61B 2018/00351* (2013.01); *A61B 2018/00577* (2013.01); *A61B 2018/00839* (2013.01); *A61B 2505/05* (2013.01); *A61N 1/37223* (2013.01); *A61N 1/37235* (2013.01)

(58) Field of Classification Search
CPC ..... A61B 5/6869; A61B 5/046; A61B 5/7235; A61B 5/0538; A61B 5/055; A61B 6/032; A61B 6/037; A61B 5/0036; A61B 5/0044; A61B 5/04011; A61B 5/7239; A61B 18/1492; A61B 5/042; A61B 2505/05; A61B 2018/00351; A61B 2018/00577; A61B 2018/00839; A61N 1/362; A61N 1/3956; A61N 1/37223; A61N 1/37235

See application file for complete search history.

(56) References Cited

U.S. PATENT DOCUMENTS

| | | | |
|---|---|---|---|
| 4,754,753 | A | 7/1988 | King |
| 5,193,550 | A | 3/1993 | Duffin |
| 5,732,708 | A | 3/1998 | Nau et al. |
| 5,741,304 | A | 4/1998 | Patwardhan et al. |
| 5,776,168 | A | 7/1998 | Gunderson |
| 6,106,460 | A * | 8/2000 | Panescu ............... A61B 5/0422 600/300 |
| 6,317,626 | B1 | 11/2001 | Warman |
| 6,345,199 | B1 | 2/2002 | Thong |
| 6,658,283 | B1 | 12/2003 | Bornzin et al. |
| 7,069,069 | B2 | 6/2006 | Fishler et al. |
| 7,123,954 | B2 | 10/2006 | Narayan et al. |
| 7,212,849 | B2 | 5/2007 | Zhang et al. |
| 7,941,205 | B2 | 5/2011 | Jung et al. |
| 8,175,709 | B2 | 5/2012 | Lian et al. |
| 8,195,281 | B2 | 6/2012 | Dal Molin et al. |
| 8,239,020 | B2 | 8/2012 | Zhang et al. |
| 8,688,200 | B2 | 4/2014 | Song et al. |
| 8,874,212 | B2 | 10/2014 | Euzen et al. |
| 9,014,806 | B2 | 4/2015 | Henry et al. |
| 9,248,295 | B2 | 2/2016 | Spinelli et al. |
| 10,363,100 | B2 | 7/2019 | Trayanova et al. |
| 2003/0083586 | A1 | 5/2003 | Ferek-Petric |
| 2004/0059237 | A1* | 3/2004 | Narayan ............ A61B 5/04525 600/509 |
| 2007/0083193 | A1* | 4/2007 | Werneth ............... A61B 5/742 606/41 |
| 2008/0071182 | A1 | 3/2008 | Cazares et al. |
| 2012/0165811 | A1* | 6/2012 | Gillberg ............... A61N 1/3702 606/41 |
| 2016/0113533 | A1 | 4/2016 | Ben-David et al. |
| 2016/0213928 | A1 | 7/2016 | Ghosh |
| 2017/0178403 | A1* | 6/2017 | Krummen ........... A61B 5/6823 |
| 2017/0319278 | A1 | 11/2017 | Trayanova et al. |
| 2018/0103865 | A1 | 4/2018 | Trayanova et al. |

\* cited by examiner

PRECISE LOCALIZATION OF CARDIAC ARRHYTHMIA USING INTERNAL ELECTROCARDIOGRAPH (ECG) SIGNALS SENSED AND STORED BY IMPLANTABLE DEVICE

CLAIM OF PRIORITY UNDER 35 U.S.C. § 119

The present application claims the benefit of priority of U.S. Provisional Patent Application Ser. No. 62/620,589, filed Jan. 23, 2018 and entitled "Precise Localization of Ventricular Arrhythmia Using Internal Electrocardiograph (ECG) Signals Sensed and Stored by Implantable Device," which is hereby incorporated by reference in its entirety.

BACKGROUND

Field of the Disclosure

The present disclosure generally relates to implantable medical devices and, more particularly, to localization of a cardiac arrhythmia using internal electrocardiograph (ECG) signals sensed by such an implantable device.

Relevant Background

Heart disease is the leading cause of death in the U.S. (about 610,000 per year) and in other developed countries and accounts for more mortality than that from all types of cancers combined. Contrary to common belief, heart attacks are not the immediate and direct cause of cardiac death. Rather, most cardiac deaths occur without warning (hence the term sudden cardiac death, or SCD), primarily from fatal ventricular arrhythmias (VAs) that originate from the ventricles. Fortunately, most of these SCDs due to VAs can now be prevented with the advent of implantable cardioverter/defibrillators (ICDs). ICD implantation is the most reliable therapy to reduce mortality from SCD as validated by a large number of randomized multi-center clinical trials. Currently, accepted clinical indications for ICD implantation include: (1) primary prevention for those patients at high risk of SCD without a prior SCD event, e.g., those with a history of major heart attacks, and (2) secondary prevention for those patients who have had an SCD event, but survived. It is worthwhile to point out that the probability to survive from an SCD event without an ICD is very low (<4% if SCD occurs outside the hospital). Many of those survivors likely suffer from brain damage and fall into a vegetative state even if he or she is resuscitated.

However, the implantation of ICDs does not prevent a fatal VA from occurring. Rather, an ICD delivers an electrical shock to the heart to "reset" the electrical activities of the ventricles in an effort to restore normal heart rhythm. Although administering shocks saves lives, these shocks often cause severe discomfort and increase morbidity in patients. Both physical and psychological trauma may ensue. Pharmacological agents (antiarrhythmic drugs) may be used to suppress these fatal VAs. However, the effectiveness of these agents is limited, and side effects are common. Catheter-based ablation—a technique using thermal energy, typically heat generated from radio frequency (RF) energy to destroy the substrates of arrhythmias—is an effective therapy for cardiac arrhythmias including VAs. During ablation, a catheter is inserted percutaneously through an artery or vein and advanced to the heart. The success of the ablation procedure depends on precise localization of the VA origin to guide the delivery of RF energy, which is the most time-consuming portion of the ablation procedure that can take 5 to 8 hours. The longer the procedure takes, the higher the probability of complications.

Body-surface lead electrocardiograph (ECG) signals are generated noninvasively from a set of electrodes (e.g., typically 10 electrodes), placed on the skin of the chest and the limbs of a patient and connected to a recording machine that measures electrical activity of the heart. The body-surface lead (or external) ECG signals recorded during VAs can be analyzed to identify the VA origin and thereby guide the ablation. Unfortunately, such ECG recordings are not available during VAs in the majority of cases. ICDs are designed to deliver electrical shock within seconds after a fatal VA is identified. During a fatal VA, there is no time to perform a surface ECG recording unless the patient is connected with an ECG recorder at all times, which is not practical. Furthermore, VA frequently causes hemodynamic collapse and should be terminated immediately. Therefore, there will not be the luxury of time to perform an ECG recording.

SUMMARY

Certain aspects of the present disclosure generally relate to determining a localization of a cardiac arrhythmia (e.g., a ventricular arrhythmia or an atrial arrhythmia) using internal electrocardiograph (ECG) signals sensed and stored by an implantable device.

Certain aspects of the present disclosure provide a method of analyzing an arrhythmia in a subject. The method generally includes reading, from an implantable device implanted in the subject, a plurality of internal ECG signals sensed and stored by the implantable device while the subject was experiencing an arrhythmia event; performing an analysis of the read internal ECG signals; and determining a localization of the arrhythmia based on the analysis.

Certain aspects of the present disclosure provide a non-transitory computer-readable medium having instructions stored thereon that, when executed by at least one processor, cause the processor to perform operations for analyzing an arrhythmia in a subject. The operations generally include reading, from an implantable device implanted in the subject, a plurality of internal ECG signals sensed and stored by the implantable device while the subject was experiencing an arrhythmia event; performing an analysis of the read internal ECG signals; and determining a localization of the arrhythmia based on the analysis.

Certain aspects of the present disclosure provide a system for analyzing an arrhythmia in a subject. The system includes a wireless communications device and at least one processor communicatively coupled to the wireless communications device. The wireless communications device is typically configured to read, from an implantable device implanted in the subject, a plurality of internal ECG signals sensed and stored by the implantable device while the subject was experiencing an arrhythmia event. The processor is generally configured to perform an analysis of the read internal ECG signals and to determine a localization of the arrhythmia based on the analysis.

Certain aspects of the present disclosure provide an implantable device for implanting in a subject. The implantable device generally includes a memory and multiple leads with a plurality of electrodes for sensing a plurality of internal ECG signals. The memory is generally configured to store the sensed internal ECG signals at least while the subject is experiencing an arrhythmia and to subsequently read out the stored internal ECG signals for analysis to determine a localization of the arrhythmia.

BRIEF DESCRIPTION OF THE DRAWINGS

So that the manner in which the above-recited features of the present disclosure can be understood in detail, a more particular description, briefly summarized above, may be had by reference to aspects, some of which are illustrated in the appended drawings. It is to be noted, however, that the appended drawings illustrate only certain typical aspects of this disclosure and are therefore not to be considered limiting of its scope, for the description may admit to other equally effective aspects.

DETAILED DESCRIPTION

Figure 1A:
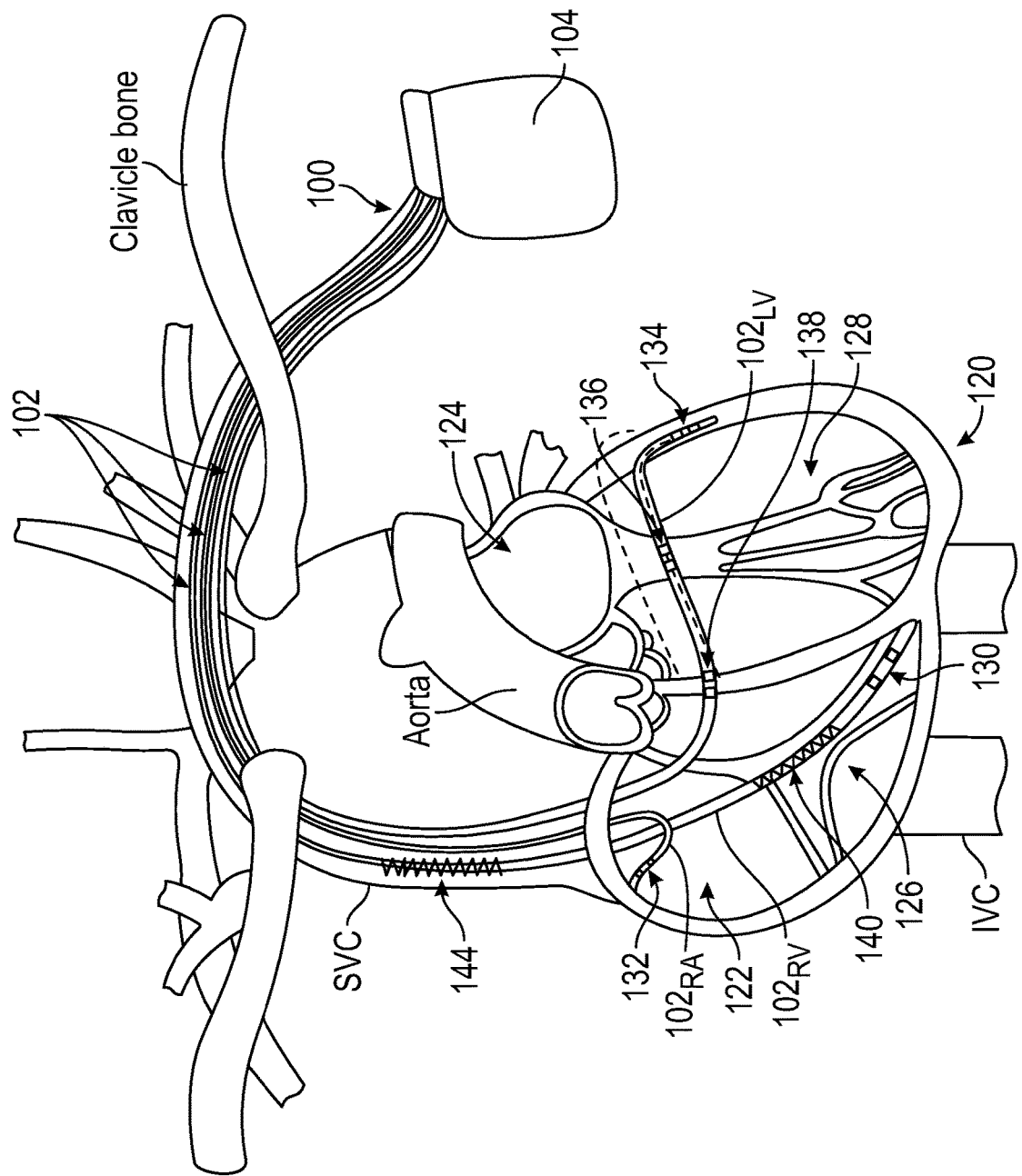
FIG. 1A illustrates an example implantable cardioverter/defibrillator (ICD) system, as an example implantable device, with leads fed through blood vessels to the heart.

Certain aspects of the present disclosure provide methods and apparatus for determining a precise localization of an arrhythmia (e.g., a ventricular arrhythmia (VA) origin or exit site) in the heart of a subject using internal electrocardiograph (ECG) signals sensed and stored by an implantable device implanted in the subject. By using internal ECG signals, as opposed to body-surface lead or external ECG signals, the localization of the arrhythmia site may be more precisely determined in an effort to more effectively treat the arrhythmia. The internal ECG signals lead to a more precise localization because the internal ECG signals are recorded from internal electrodes placed closer to the signal source and whose anatomic locations are registered in reference to the heart, as compared to the external or body-surface lead ECG signals that are recorded from body-surface electrodes placed more remotely from the heart and at standard anatomic locations in reference to the torso, not to the heart (which represents a significant source of error due to individual variations in orientation of the heart within the chest). Certain aspects of the present disclosure may be active or operational in any setting (e.g., outpatient or inpatient) where the implantable device is present in the subject's body, regardless whether the subject is ambulatory, at rest, or restrained during a medical procedure (e.g., an ablation procedure).

The present disclosure utilizes non-limiting examples of ventricular arrhythmia (VA) to illustrate various aspects of this disclosure in the text and in the accompanying drawings. It should be noted that the same approaches are applicable to atrial arrhythmia (AA), except the atrial electrogram complexes, 3-D atrial geometry, and/or tissue characteristics of the atrial myocardium will be used instead of those for the ventricles.

Various aspects of the disclosure are described more fully hereinafter with reference to the accompanying drawings. This disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein, one skilled in the art should appreciate that the scope of the disclosure is intended to cover any aspect of the disclosure disclosed herein, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure, functionality, or structure and functionality in addition to or other than the various aspects of the disclosure set forth herein. It should be understood that any aspect of the disclosure disclosed herein may be embodied by one or more elements of a claim.

As used herein, the term "determining" encompasses a wide variety of actions. For example, "determining" may include calculating, computing, processing, deriving, investigating, looking up (e.g., looking up in a table, a database, or another data structure), ascertaining, and the like. Also, "determining" may include receiving (e.g., receiving information), accessing (e.g., accessing data in a memory), and the like. Also, "determining" may include resolving, selecting, choosing, establishing, and the like.

As used herein, the term "subject" may refer to a human or another animal, such as a pig or a dog.

Example Implantable Device

Implantable devices may include any device capable of being implanted in a subject's body. Examples of an implantable device include an implantable cardioverter/defibrillator (ICD), a pacemaker, an internal electrocardiograph (ECG) recording device, and the like.

FIG. 1A illustrates an ICD system 100 as an example of an implantable device for use with certain aspects of the present disclosure. Although the term "ICD" is used throughout this disclosure for ease of explanation, the reader is to understand that the term "ICD" may be replaced by "implantable device" throughout and that certain aspects of the present disclosure may be implemented by any suitable implantable device capable of performing similar functions related to arrhythmia localization techniques as described herein.

As depicted in FIG. 1A, the ICD system 100 comprises a generator 104 connected with leads 102 fed through blood vessels to various positions of the heart 120. FIG. 1A illustrates a four-chambered heart 120 with a right atrium (RA) 122, a left atrium (LA) 124, a right ventricle (RV) 126, and a left ventricle (LV) 128. Although a four-chambered heart is illustrated in FIG. 1A as a non-limiting example, aspects of the present disclosure may also apply to a heart with more or less than four chambers (e.g., a three-chambered heart), for a different species.

Figure 1B:
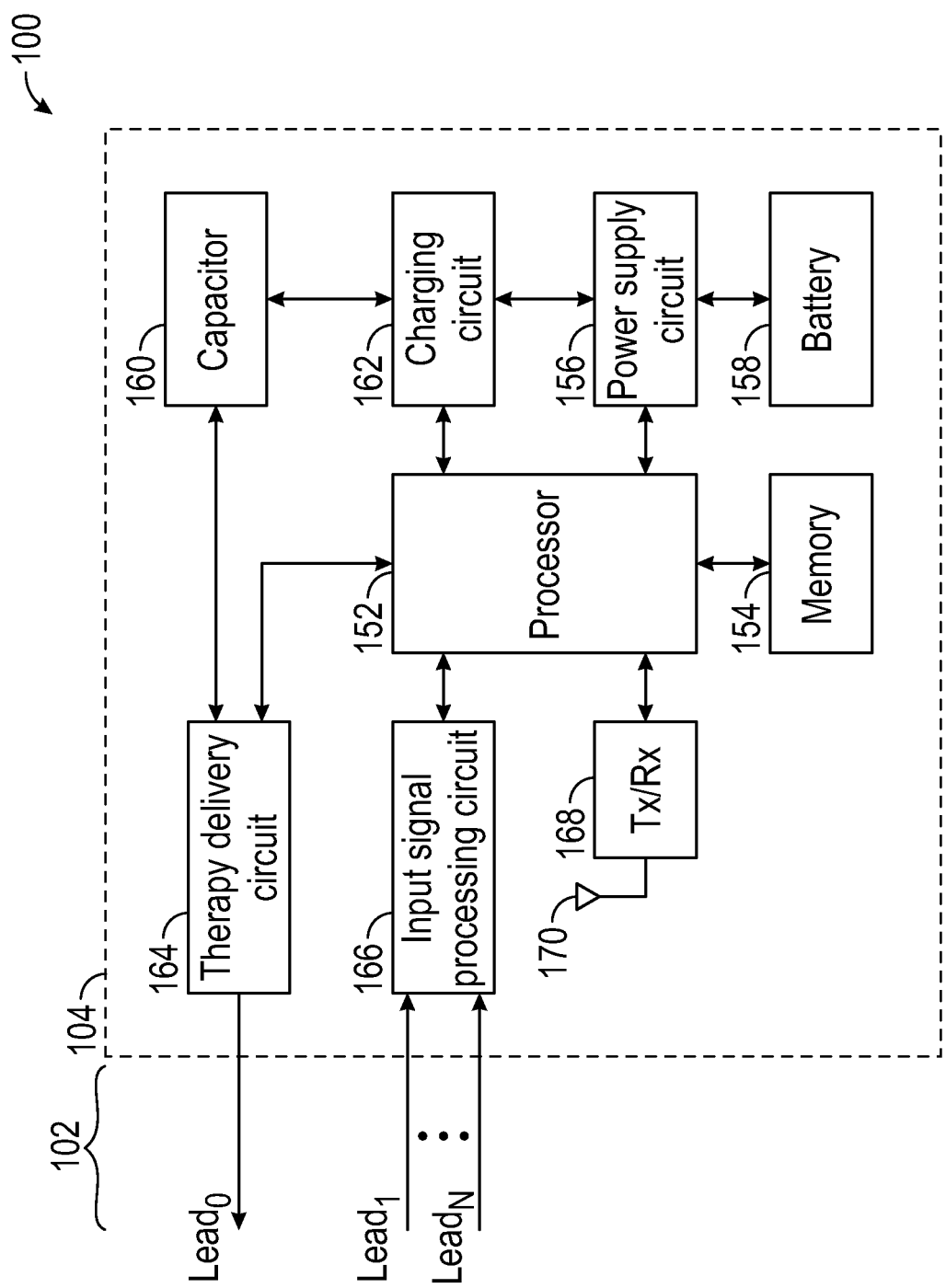
FIG. 1B is an example block diagram of the ICD system of FIG. 1A.

The generator 104 may include a hermetically sealed housing (e.g., a can made of metal, such as titanium). The housing may contain integrated circuits (ICs), a battery 158, a capacitor 160 for storing charge and delivering a shock, and other electrical and mechanical hardware, some of which is illustrated in FIG. 1B. The ICs may include, for example, a processor 152, memory 154 coupled to the processor, analog circuitry, digital circuitry, mixed-signal circuitry (with both digital and analog components), programmable logic devices (e.g., field-programmable gate arrays (FPGAs)), and/or application-specific integrated circuits (ASICs). The processor 152 may read data and instructions from and write data to the memory 154. The generator 104 may include a power supply circuit 156 coupled to the battery 158 and to various circuits, such as the processor 152 and a charging circuit 162. The power supply circuit 156 may be implemented as a DC-to-DC converter for converting the battery voltage to one or more voltage levels for the various circuits. The charging circuit 162 may include a transformer and may be controlled by the processor 152 to charge the capacitor 160 for delivering a therapeutic shock. The generator 104 may also include a therapy delivery circuit 164 and an input signal processing circuit 166. The therapy delivery circuit 164 may receive energy from the capacitor 160 and deliver a shocking pulse to the heart 120 via one or more shocking coils (e.g., distal coil 140 or proximal coil 144), typically on the RV lead(s) 102 and the housing (e.g., metallic can) of the generator 104. The therapy deliver circuit 164 may be activated or otherwise controlled by the processor 152. The input signal processing circuit 166 may receive internal ECG signals from the electrodes (e.g., 130, 132, 134, 136, 138) that are embedded in a plurality of leads 102 (e.g., lead$_1$, lead$_2$, . . . lead$_N$) and process these signals (e.g., via amplifying, filtering, converting the analog signals to digital signals, and/or extracting certain features, either digitally or in the analog domain) for analysis by the processor 152 and/or recording in the memory 154. For example, the processor 152 may recognize that the internal ECG signals are indicative of an arrhythmia event (e.g., a ventricular arrhythmia (VA) event or an atrial arrhythmia event) and may write the internal ECG signals (or a representation thereof) to the memory 154 to capture the arrhythmia event for subsequent analysis. The generator 104 may also include a transceiver (Tx/Rx) 168 and at least one antenna 170 for wireless communications between the ICD system 100 and an external device, such as an ICD programmer. The transceiver 168 may be coupled to the processor 152 for receiving signals from the processor for transmission via the antenna 170 and for sending signals received by the antenna and processed by the transceiver to the processor. For example, the transceiver 168 and antenna 170 may be responsible for communicating recorded internal ECG signals indicative of an arrhythmia event to the external device.

The leads 102 may be wires with one or more electrodes embedded on at least some of the leads. Although three leads 102 (e.g., a right atrial lead $102_{RA}$, a right ventricular lead $102_{RV}$, and a left ventricular lead $102_{LV}$) are illustrated in FIG. 1A as a non-limiting example, aspects of the present disclosure may use more or less than three leads (e.g., two leads). The ICD generator 104 is typically implanted subcutaneously in either the left or the right pectoral area. For certain aspects, the ICD generator 104 may alternatively be implanted subcutaneously in the upper abdomen. The ICD leads 102 are connected to the generator 104 at one end and inserted into various heart chambers (e.g., the right atrium 122 and the right ventricle 126) at the other end (e.g., through the subclavian or axillary vein) or inserted into epicardial aspects of the left ventricle 128 through the coronary sinus and its branches around the heart. For example, at least some of the electrodes on the ICD leads 102 are used to deliver electric current, for example, either to excite or to pace the heart muscle (similar to a pacemaker) or to stun or to shock the heart to reset a fatal VA with high electrical energy (e.g., defibrillation or ICD shocks). At least some of the electrodes on the ICD leads 102, which may be the same or different from the electrodes used for delivering current, are used to sense the electrical activities of the heart 120.

Certain aspects of the present disclosure utilize electrodes on the ICD leads to monitor the electrical activities of the atria and/or ventricles (e.g., continuously throughout ICD battery lifetime) during normal rhythm and during arrhythmias (e.g., ventricular tachycardia (VT)). The electrodes may be located on the existing set of leads 102 associated with the ICD function and/or may be located on one or more additional leads. The electrodes may be either intracorporal (inside the various parts of the body, but outside of the heart) and/or intracardiac (inside the heart itself). The intracorporal and/or intracardiac signals sensed by these electrodes, in either bipolar or unipolar configurations, may be referred to as internal electrocardiograph (ECG) signals and may be stored in the memory 154 inside the generator 104. Unipolar configurations refer to electrode signals referenced to a common electrode signal, whereas bipolar configurations refer to signal differences between two electrodes.

For example, the RV lead $102_{RV}$ may include a pair of electrodes 130 located at or near the distal end of the RV lead, as illustrated in FIG. 1A. Likewise, the RA lead $102_{RA}$ may include a pair of electrodes 132 located at or near the distal end of the RA lead, as illustrated in FIG. 1A. The LV lead $102_{LV}$ may be fed through the coronary sinus and may include a set of electrodes 134 (e.g., two to four electrodes) located at or near the distal end of the LV lead. For certain aspects, the LV lead $102_{LV}$ may include a pair of electrodes 136 located in the vicinity of the middle portion of the coronary sinus and more proximally than the distal end of the LV lead and/or a pair of electrodes 138 located at or in close proximity to the coronary sinus and even more proximally along the LV lead than the pair of electrodes 136. The electrodes 130, 132, 134, 136, and 138 may be employed as sensing and/or pacing electrodes by the ICD system 100. In addition to the sensing electrodes, the leads 102 may include one or more shocking electrodes. For example, the RV lead $102_{RV}$ may include a distal defibrillation coil 140, which may be positioned in the right ventricle 126, as illustrated in FIG. 1A. For certain aspects, the RV lead $102_{RV}$ may include a proximal defibrillation coil 144, which may be positioned in the superior vena cava (SVC). For certain aspects, either or both coils 140 and 144 may serve as a sensing electrode and as a pacing electrode.

Compared to external body-surface ECG signals captured by electrodes external to the body, internal ECG signals offer several advantages. For example, internal ECG signals are sensed by electrodes: (1) placed closer to the source of the cardiac electrical activity; (2) having less signal loss and thereby better signal-to-noise ratio (SNR) because the electrical signals need not pass through the intervening tissues (e.g., the lungs and fat tissue) between the heart and the body-surface electrodes of the conventional external ECG, which function as low-pass filters and attenuate the signals of the external body-surface ECG; and (3) having a more consistent placement, since individual subjects, even within a species, have different body shapes, leading to varied placement of surface ECG electrodes in reference to the individual's heart. By using quantitative analysis techniques, one or more mathematic models may be used to "calculate" or predict the precise localization of the arrhythmia origin (e.g., in the case of a focal VA) or arrhythmia exit (in the case of a re-entrant VA) site based upon the recorded internal ECG signals from these electrodes embedded on the implanted leads.

For example, a patient with an implanted ICD may be seen at a hospital or clinic with a history of electrical shock(s) from the ICD. The patient may present with a normal cardiac rhythm, so measuring body-surface ECG signals at that time is of little value for determining any arrhythmias the patient previously experienced. Instead, an external device—such as an ICD programmer and the like that are capable of wirelessly communicating with the ICD for performing data transfer, using communication technologies such as a telemetry wand, WiFi, or Bluetooth®—may be used to extract the previously recorded internal ECG signals from the ICD (i.e., signals that occurred in the past, such as during a VA). A quantitative analysis of the internal ECG signals may be performed to determine a precise localization of the arrhythmia origin or exit site (e.g., with a resolution of 2.0 cm or better, such as around 0.5 cm).

Certain portions of the quantitative analysis may be performed, for example, by one or more processors in the ICD system 100, by one or more external processors after the signals are read from the ICD system, by one or more processors in another implantable device (e.g., a second device in addition to the ICD system), or by a combination of ICD, external, and/or other implantable device processors. The processing system may be implemented as a specific standalone system or as part of a more complex system, such as a hardware system used during an ablation procedure (e.g., a multi-channel electrophysiology recording system or a three-dimensional mapping system). For certain aspects, the quantitative analysis may utilize one or more images (e.g., three-dimensional (3-D) images) of the subject's heart and of the anatomic locations of the recording electrodes (in reference to the subject's heart). The image(s) may be generated by any of various suitable imaging modalities, such as computed tomography (CT), magnetic resonance imaging (MRI), cardiac nuclear scans with radioactive isotopes such as thallium or sestamibi, echocardiography, or positron emission tomography (PET)) performed on the patient with the ICD implanted therein and/or prior to implantation. For certain aspects, data on the geometry of the heart and tissue characteristics of the myocardial tissues and anatomic information on the locations of the electrodes may be extracted from the image(s) and may be utilized in the quantitative analysis. For certain aspects, the quantitative analysis may involve any of various suitable techniques for deriving the location of the origin or exit site of the arrhythmia using the recorded internal ECG signals (and the electrode locations), such as vector analysis, conduction time analysis, morphology matching either in the time or frequency domain, frequency spectrum characteristics, amplitude and timing information of the local near-field electrograms, analysis of far-field electrograms, or a combination of two or more of these and other techniques for identification and interpretation. Example quantitative analysis techniques for deriving the location of the arrhythmia origin or exit site are described in more detail below.

Once the arrhythmia origin or exit site has been precisely located, treatment (e.g., ablative treatment) may be administered. For example, an ablation catheter may be guided to the determined arrhythmia origin or exit site, and ablation of the heart tissue may be performed at that site. For other aspects, the same or a different quantitative analysis technique may be performed one or more times with the ablation catheter inserted in an effort to refine the localization of the arrhythmia origin or exit site, just before ablating the tissue.

Figure 2:
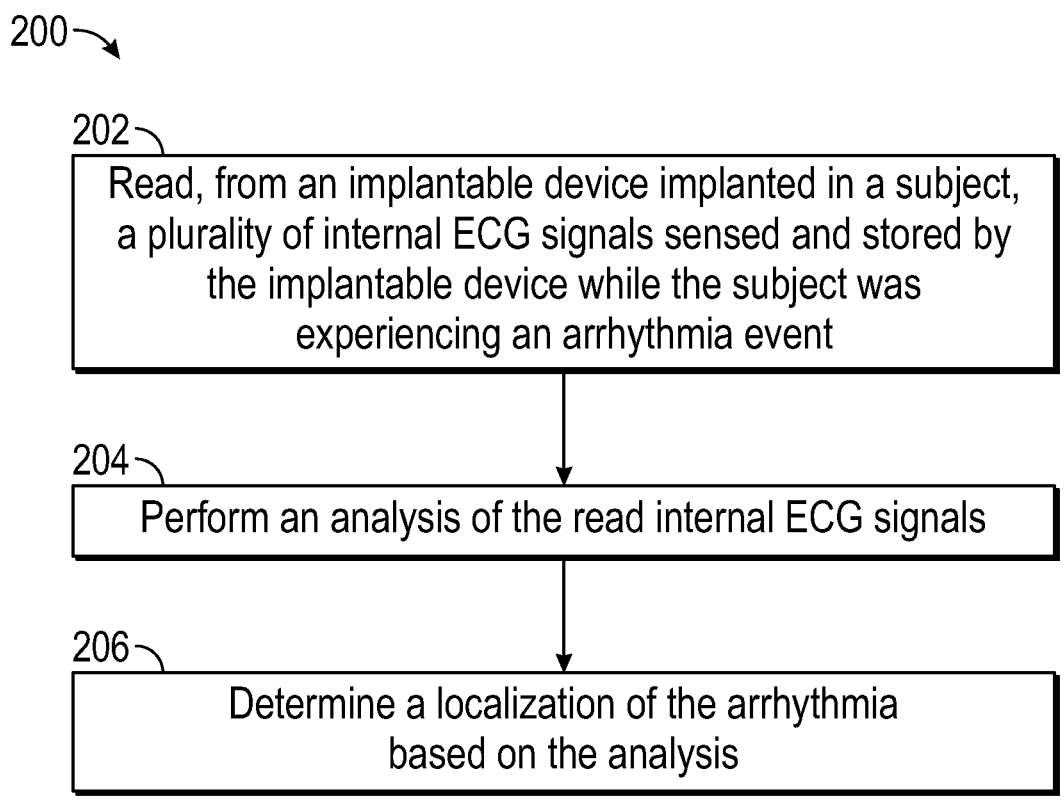
FIG. 2 is a flow diagram of example operations for analyzing an arrhythmia, in accordance with certain aspects of the present disclosure.

Example Operations for Analyzing Internal ECG Signals Sensed and Stored During an Arrhythmia FIG. 2 is a flow diagram of example operations 200 for analyzing a cardiac arrhythmia (e.g., an atrial arrhythmia or a ventricular arrhythmia (VA)) in a subject (e.g., a human patient or another animal), in accordance with certain aspects of the present disclosure. At least some of the operations 200 may be performed by any suitable system with a wireless communications device (e.g., telemetry via radio frequency (RF) signals, such as Bluetooth®, WiFi, or other radio access technologies) and one more processors coupled to the wireless communications device and configured to read signals received from an implantable device via the wireless communications device. For example, the system may include a programmer that communicates with an ICD through wireless communication methods, such as Bluetooth® technology, RF signals, or other telecommunication technologies.

The operations 200 may begin, at block 202, by reading a plurality of internal electrocardiograph (ECG) signals from an implantable device implanted in the subject. The plurality of internal ECG signals were sensed and stored by the implantable device, at any time while the subject was experiencing an arrhythmia event (e.g., while the subject was ambulatory and experiencing an arrhythmia event). As used herein, the term "ambulatory" generally refers to being capable of walking, either independently or with assistance, as opposed to, for example, being constrained to an operating table.

At block 204, an analysis of the read internal ECG signals may be performed (e.g., by the same system that read the internal ECG signals). At block 206, a localization of the arrhythmia may be determined based on the analysis (e.g., by the same system that read the internal ECG signals).

According to certain aspects, the operations 200 may further entail guiding (or assisting guidance of) a catheter inserted into the subject to the determined localization of the arrhythmia and performing ablation of heart tissue of the subject at the localization using the catheter. For certain aspects, the operations 200 may further involve delivering, via a roving catheter, electrical (pacing) stimulations at multiple sites in one or more chambers of a heart of the subject; sensing another plurality of internal ECG signals during the delivery of the electrical stimulations; and analyzing differences between the other plurality of internal ECG signals (from the pacing) and on the plurality of internal ECG signals sensed and stored by the implantable device. For certain aspects, the operations 200 may further entail refining the localization of the arrhythmia based on the analysis. In this case, the ablation may be performed on the refined localization of the arrhythmia.

According to certain aspects, the operations 200 may further involve employing a catheter inserted into a heart of the subject to create internal ECG footprints or templates, by pacing stimulations at various sites in the subject's heart, that are to be used as reference points for the analysis of the internal ECG during arrhythmia in order to improve the spatial accuracy in determining the localization of the arrhythmia.

According to certain aspects, the implantable device is capable of administering an electric shock to a heart of the subject. In this case, the implantable device may include an implantable cardioverter/defibrillator (ICD). For other aspects, the implantable device includes a pacemaker, an internal ECG device, or other implantable medical device.

According to certain aspects, the implantable device may have multiple leads with a plurality of electrodes for sensing the internal ECG signals. For certain aspects, the implantable device comprises at least two leads with at least four electrodes. For other aspects, the implantable device comprises a suitable number of leads (with embedded electrodes) for determining the localization of the arrhythmia at block 206 with a desired precision.

According to certain aspects, there is a delay between a time when the internal ECG signals were stored during or resulting from an arrhythmia event and a time of the reading at block 202 (e.g., data retrieving). For example, the delay may be a few minutes or greater than a few hours, one day, or longer.

According to certain aspects, the determined localization has a spatial resolution of 2.0 cm or better (e.g., 0.5 cm), as compared to the typical ablation lesion size of 0.4 to 0.6 cm in diameter.

According to certain aspects, performing the analysis at block 204 involves performing a vector analysis of the internal ECG signals. For certain aspects, performing the analysis at block 204 further includes determining locations of a plurality of electrodes implanted in the subject, associated with the implantable device, and used to sense the internal ECG signals. In this case, performing the vector analysis may entail performing the vector analysis based on the determined locations of the plurality of electrodes. For certain aspects, determining the locations of the electrodes involves performing a computed tomography (CT) scan, a magnetic resonance imaging (MRI) scan, or one or more other imaging modalities of the subject.

According to certain aspects, performing the analysis at block 204 entails performing a conduction time analysis of the internal ECG signals. For certain aspects, conduction time analysis may utilize the data on tissue characteristics of the myocardium obtained from computed tomography (CT) scan, a magnetic resonance imaging (MRI) scan, a positron emission tomography (PET) scan, a nuclear scan with isotopes such as thallium, and/or one or more other imaging modalities of the subject. For certain aspects, these 3-D cardiac imaging modalities may be employed alone or in combination and may be performed before or after the ICD implantation.

According to certain aspects, the subject is a human patient. For other aspects, the subject may be a pig or a dog, for example.

According to certain aspects, the implantable device may store the internal ECG signals and derivatives thereof, which may be processed in either digital or analog forms, during single or multiple arrhythmia events that can originate from single or multiple cardiac sites for comparison, analysis, and localization of the arrhythmia(s) by medical personnel during device interrogation.

According to certain aspects, performing the analysis at block 204 involves performing the analysis based on derivatives (e.g., dV/dt) of the sensed internal ECG signals.

According to certain aspects, the operations 200 further entail receiving one or more tissue characteristics (e.g., myocardial tissue characteristics) of the heart of the subject. In this case, performing the analysis at block 204 may involve performing the analysis of the read internal ECG signals and the received tissue characteristics. The one or more tissue characteristics may include any of various suitable characteristics intrinsic to the myocardium that may affect the conduction of the activation wave front in the heart. For certain aspects, the one or more tissue characteristics include at least one of a scar content, an ischemic score, or a degree of myocardial edema.

According to certain aspects, the operations 200 may further involve reading, from the implantable device implanted in the subject, another plurality of internal ECG signals sensed and stored by the implantable device while the subject was experiencing another arrhythmia event; performing an analysis of the other plurality of internal ECG signals; determining a localization of another arrhythmia based on the analysis of the other plurality of internal ECG signals; and comparing the localization of the arrhythmia and the localization of the other arrhythmia to determine that the localizations comprise a same site in a heart of the subject.

Example Quantitative Analysis Techniques for Arrhythmia Localization

As described above, an external device (e.g., an ICD programmer or other processing system) may perform a quantitative analysis of internal ECG signals received from an implantable device and imaging data and then determine a localization of an arrhythmia origin or exit site based on the analysis. The following paragraphs describe the general approach in greater detail and provide two different example analysis techniques: (1) vector analysis and (2) conduction time analysis.

The general approach involves first determining the positions and configurations of the electrodes (e.g., electrodes 130, 132, 134, 136, and/or 138) used to sense the internal ECG signals for a particular subject. For example, the right ventricular lead $102_{RV}$ may have two electrodes (e.g., the pair of electrodes 130) at or near its distal tip: RVd1 (most distal electrode, also referred to as the RV apex electrode) and RVd2 (very close but slightly more proximal to RVd1). The RV lead $102_{RV}$ may also have one or two shocking coils (e.g., coils 140 and/or 144): RVdcoil (distal ICD shocking coil, usually located in the right ventricle) and RVpcoil (proximal ICD shocking coil, usually located in the superior vena cava (SVC), which may be absent in some ICD systems). For certain aspects, the shocking coils may also serve as recording electrodes for sensing internal ECG signals.

The right atrial (RA) lead $102_{RA}$ may have two electrodes (e.g., the pair of electrodes 132) at or near its tip: RA1 and RA2, with RA1 being the more distal one by convention. The coronary sinus (CS) lead (e.g., LV lead $102_{LV}$) has a set of electrodes (e.g., two to four electrodes 134) on its distal end: CSd1, CSd2, CSd3, and CSd4, with CSd1 being the most distal one by convention. Certain aspects of the present disclosure may also include two additional electrodes (e.g., electrodes 138) located at or near the CS ostium: CSp1 and CSp2, with CSp2 being the more proximal one by convention. Certain aspects of the present disclosure may also include two additional electrodes (e.g., electrodes 136) at a middle portion of the LV lead $102_{LV}$, usually located in the middle of the main trunk of the coronary sinus: CSm1 and CSm2, with CSm2 being the more proximal one by convention.

The ICD system may also include a reference electrode, which may also be referred to as a common electrode or an indifferent electrode (IE), for unipolar recordings. For example, the reference electrode may be located at a very proximal portion (in the left subclavian vein or even the left axillary vein) of the RV lead, the CS lead, or, more likely on the RA lead or on a separate lead (e.g., an inferior vena cava (IVC) lead) that may be inserted and positioned in the IVC. Alternatively, the housing of the generator 104 (e.g., the ICD can) may serve as the reference electrode. For other aspects, a virtual reference electrode, similar in concept to a Wilson Central Terminal, may be derived from the average of three or more electrodes described above and effectively serve as the reference "electrode."

Any two of the electrodes described above may form a pair to record bipolar internal ECG signals. For electrode pairs not adjacent to each other, by convention, the more superior, anterior, and leftward electrode will bear the positive polarity, and the other electrode will bear the negative polarity. These bipolar configurations may be used to record far-field bipolar internal ECG signals. For electrodes pairs immediately adjacent to each other, typically on the same lead (e.g., CSp1 and CSp2), the more distal electrode will bear the positive polarity, and the more proximal electrode will bear the negative polarity. These directly adjacent bipolar configurations may be used to record near-field bipolar internal ECG signals.

The unipolar and far-field bipolar internal ECG signals may be used for detection of the onset of arrhythmia and its vectors, while the near-field bipolar internal ECG signals may be used for detection of the timing of local activation (i.e., the local activation time (LAT)) of the myocardium immediately underneath the bipolar pair of electrodes that are in close proximity to each other. As a non-limiting example, one of the methods to define LAT is to use the maximum dV/dt of the unipolar or far-field bipolar internal ECG as the time marker for the timing of local activation, where V(t) denotes the amplitude of the internal ECG in millivolts with time t in seconds and where dV/dt is the first derivative of V(t).

The general approach also involves establishing an individualized 3-D coordinate system, particular to the individual subject. One example coordinate system may be set up by first defining the location of the most distal electrode on the RV (e.g., RVd1) as the origin (0,0,0) of the coordinate system. Then, an X-axis may be defined as the straight line passing through the origin (RVd1) and the location of the most distal coronary sinus or LV electrode (e.g., CSd1, whose coordinates are XCSd,0,0 where XCSd is the linear distance between RVd1 and CSd1). The XZ-plane may then be considered as the plane that is defined by three points: the origin (RVd1), CSd1, and the location of the most proximal coronary sinus electrode (e.g., CSp2) at or near the CS ostium. Then, the Z-axis may be defined as the straight line that passes through the origin (RVd1) in the XZ-plane and perpendicular to the X-axis. The Y-axis may then be defined as the straight line passing through the origin (RVd1) that is perpendicular to the XZ-plane. All other locations, including those of other electrodes, atrial anatomic sites, ventricular anatomic sites, and/or arrhythmia sites, will be defined by their projections onto the above described X, Y, and Z coordinate system.

To set up the coordinate system, the actual positions of the electrodes for a particular subject may be determined based on 3-D cardiac imaging modalities and/or other localizing modalities including, but not limited to, the electroanatomical mapping and integration thereof with live fluoroscopy or computed tomography (CT) scan which may enable the registration of electrode positions intra-operatively during ICD implantation or after the implantation when the electrodes are accessible. These imaging modalities may include, but are not limited to, cardiac CT, computed tomography angiography (CTA), cardiac magnetic resonance imaging (MRI), magnetic resonance angiography (MRA), positron-emission tomography (PET), 3-D ultrasound, and the like, which provide the anatomic boundaries for the quantitative analyses of internal ECG data.

For certain aspects, the quantitative analysis may involve defining tissue characteristics of the myocardium with information derived from cardiac imaging, including but not limited to CT, MRI, PET, nuclear isotope scans, and echocardiography, in addition to the geometric data of the heart and the anatomic locations of the electrodes. For certain aspects, the quantitative analysis may, based on these derived tissue characteristics, quantify and calculate the conduction property of the volume elements (voxels) of the myocardium.

Example Vector Analysis

Based on the individualized 3-D coordinate system established above, an example vector analysis technique for localizing the arrhythmia origin or exit site based on previously recorded internal ECG signals during an arrhythmia event is presented below. Although this particular example vector analysis is explained below with respect to localizing a ventricular arrhythmia (VA) origin or exit site, those of ordinary skill in the art will understand that this technique may also be applied to localizing an atrial arrhythmia site.

This vector analysis may begin by determining an initial or first phase of VA activation (referred to as "Phase$_0$"). The earliest time point (VA initiation time or T$_0$) when any deflection (positive or negative) among all the unipolar and far-field bipolar internal ECG signals during the VA event is detected is defined as the time of initiation of VA or the beginning of Phase$_0$. The earliest time point (T$_1$) when the first derivative (dV/dt) of any unipolar or far-field bipolar internal ECG signals during VA reaches zero (i.e., amplitude of signal V(t) is a local maximum) is defined as the end of the initial phase (Phase$_0$) of activation during VA. T$_1$ represents the moment when the activation wave front begins to bend or change direction.

Figure 3:
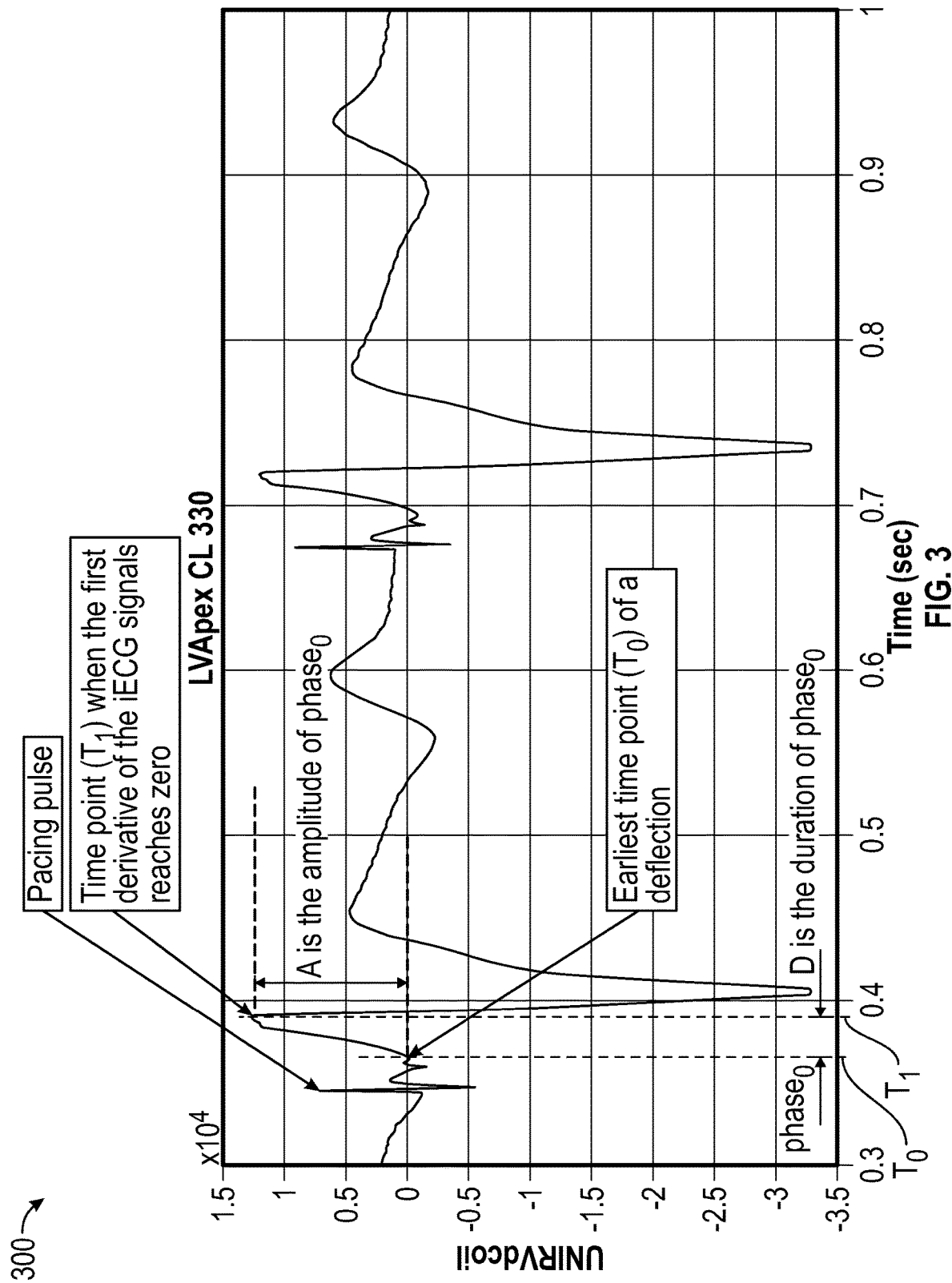
FIG. 3 is a plot of an example unipolar internal electrocardiograph (ECG) signal with time, in accordance with certain aspects of the present disclosure.
Figure 4A:
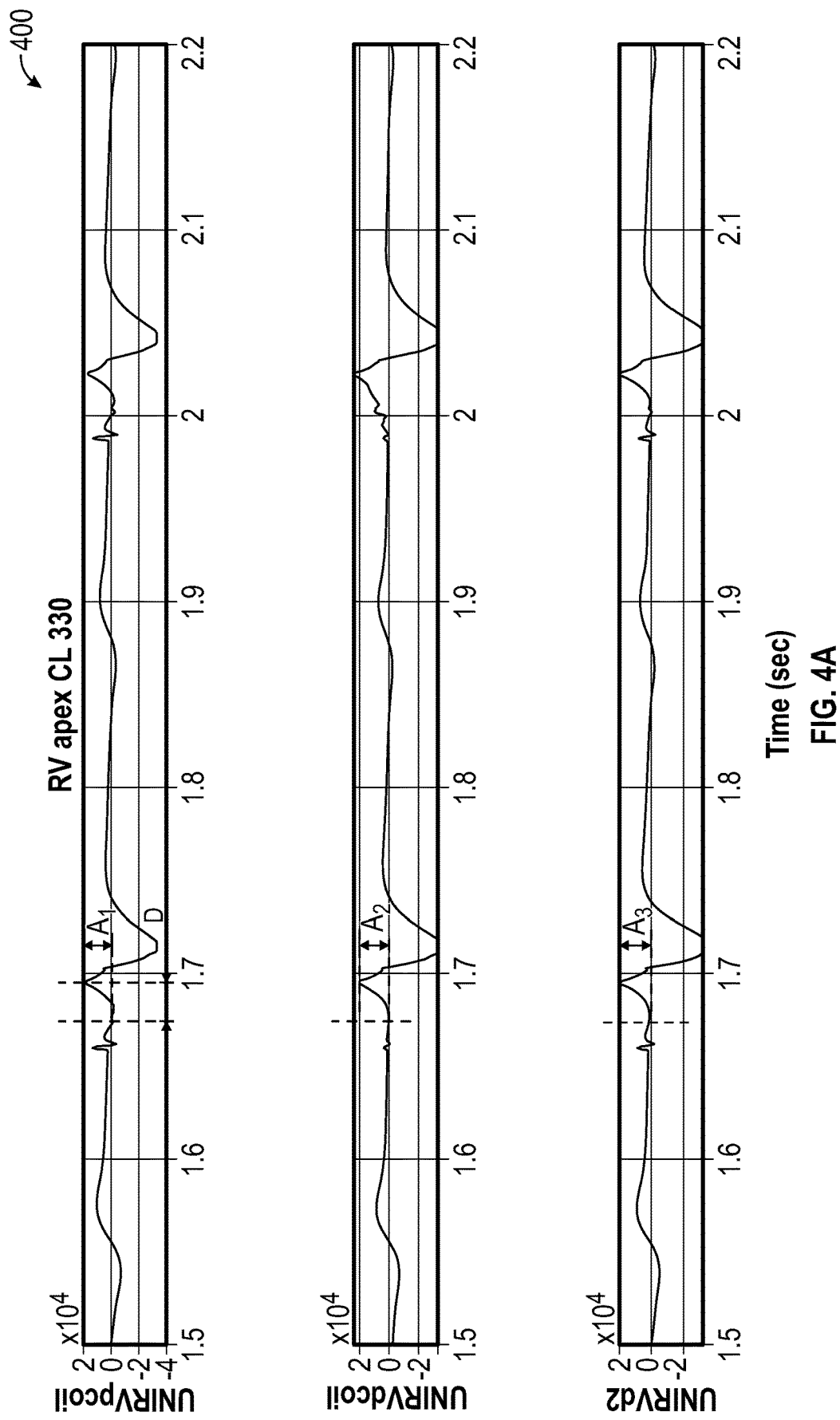
FIG. 4A provides plots of example unipolar internal ECG signals with time, illustrating different amplitudes being sensed for the same phase, in accordance with certain aspects of the present disclosure.
Figure 4B:
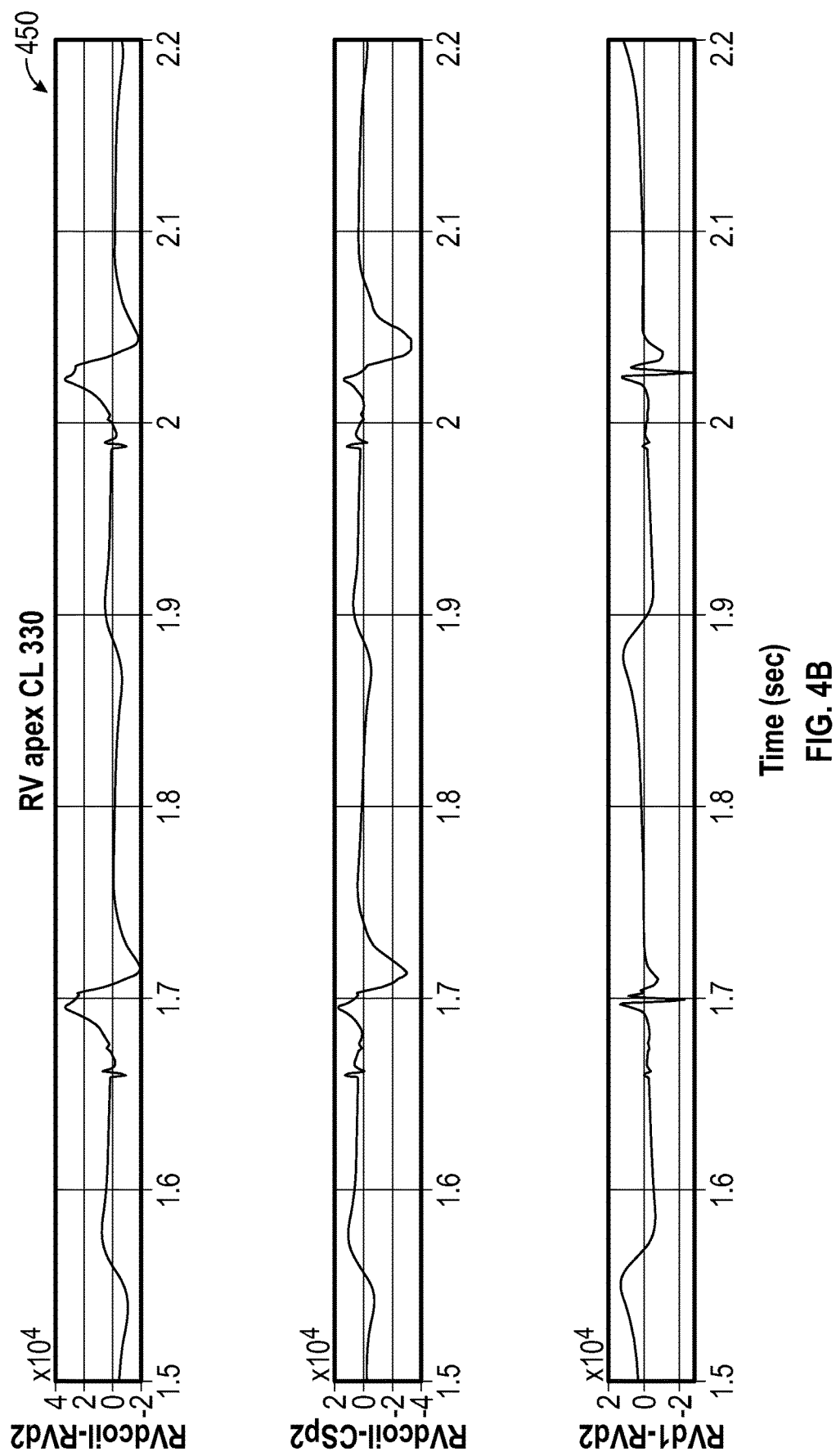
FIG. 4B provides plots of example bipolar internal ECG signals with time, in accordance with certain aspects of the present disclosure.

The time interval between T$_0$ and T$_1$ denotes the initial phase (Phase$_0$) of VA activation during which the direction of the VA vector remains essentially unchanged. FIG. 3 is a plot 300 of an example unipolar internal ECG signal (e.g., UNIRVdcoil, which is the RVd1 electrode sensed with respect to the reference electrode) with time, illustrating T$_0$, T$_1$, and Phase$_0$, in accordance with certain aspects of the present disclosure. FIG. 4A provides plots 400 of three example unipolar internal ECG signals (namely, UNIRVpcoil, UNIRVdcoil, and UNIRVd2) with time, whereas FIG. 4B provides plots 450 of three example bipolar internal ECG signals (namely, RVdcoil-RVd2, RVdcoil-CSp2, and RVd1-RVd2), in accordance with certain aspects of the present disclosure. In FIGS. 3, 4A, and 4B, the pacing pulses are followed by internal ECG signals that had an initial positive deflection followed by a negative deflection. FIGS. 3 and 4A also illustrate measurements of A and D for the internal ECG signals, where A is the amplitude of the deflection during Phase$_0$ and D is the duration of Phase$_0$ that starts at T$_0$ and ends at T$_1$.

After determining Phase$_0$ for the internal ECG signals, the next step in the vector analysis involves determining the internal ECG vector matrix (Vector$_0$) during the initial phase of VA. The vector matrix Vector$_0$ is derived from multiple unipolar internal ECG signals over the same time period, some of which are illustrated in the plots 400 of FIG. 4A. The vector amplitudes of Phase$_0$ for each signal are marked as A$_1$, A$_2$, and A$_3$. In the plots 400, note that A$_1$≠A$_2$≠A$_3$. For comparison, two example far-field bipolar internal ECG signals from RVdcoil-RVd2 and RVdcoil-CSp2 and one example near-field bipolar recording from RVd1-RVd2 are illustrated in the plots 450 of FIG. 4B. These plots 450 were obtained during the same study as the plots 400 of FIG. 4A. The directions of the individual vectors are determined by the anatomic locations of their respective electrodes.

Figure 5:
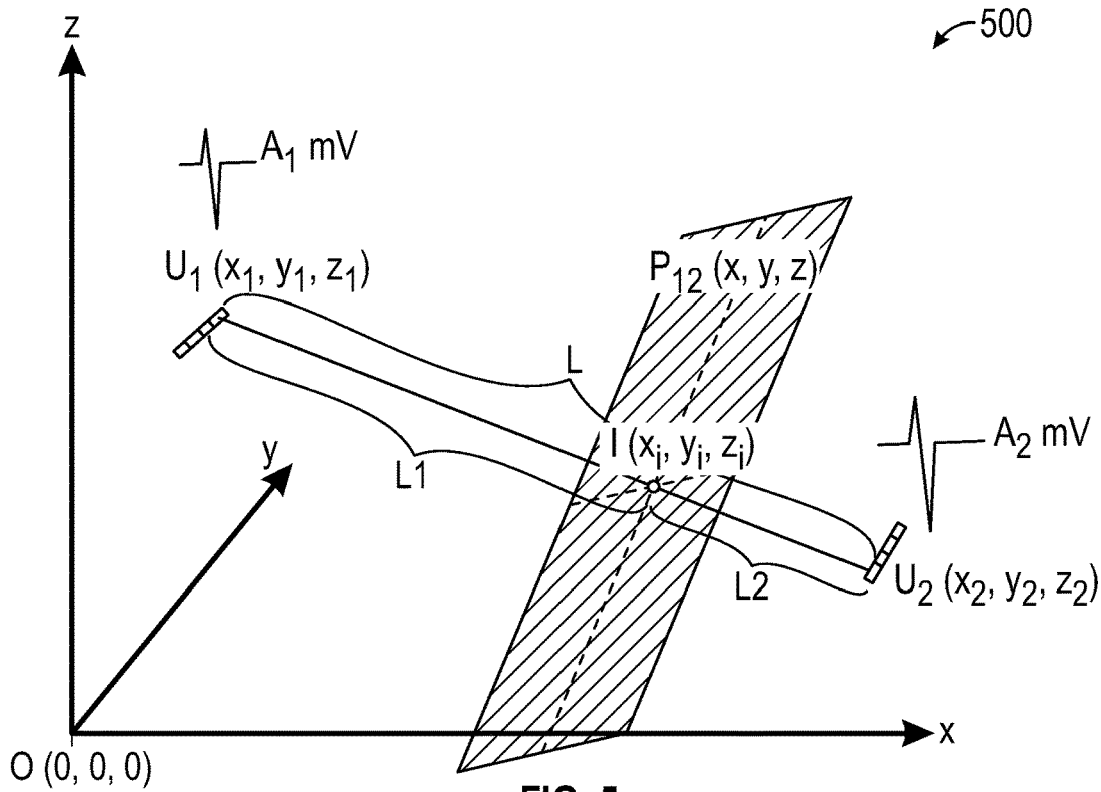
FIG. 5 is a graph illustrating determination of a plane perpendicular to a line connecting two example unipolar recording sites, in accordance with certain aspects of the present disclosure.

FIG. 5 is a graph 500 illustrating determination of a plane P$_{12}$(x,y,z) perpendicular to a line connecting two unipolar recording sites, in accordance with certain aspects of the present disclosure. To simply the description, instead of using specific unipolar recording sites (e.g., UNIRVpcoil or UNIRVdcoil), FIG. 5 uses the more general terms U$_1$ and U$_2$ to refer to any two unipolar recording sites. Based on the 3-D coordinate system laid out above, the graph 500 depicts two unipolar recording sites at U$_1$(x$_1$, y$_1$, z$_1$) and U$_2$(x$_2$, y$_2$, z$_2$). The amplitudes of their internal ECG signals during Phase$_0$ are A$_1$ and A$_2$, respectively. Accordingly, the distance L of line U$_1$U$_2$ (a vector) connecting U$_1$ and U$_2$ is defined by the following equation:

$$L = \sqrt[2]{(x_2-x_1)^2+(y_2-y_1)^2+(z_2-z_1)^2} \quad \text{Equation 1}$$

Based on electrophysiology, the source that generates the internal ECG signals of U$_1$ and U$_2$ can be anywhere in the plane P$_{12}$(x, y, z) perpendicular to line U$_1$U$_2$ with intercept I(x$_1$, y$_1$, z$_1$). Because L1 and L2 are defined by an intercept ratio as $$\begin{cases} L1 = \dfrac{A_2}{A_1+A_2}L \\ L2 = \dfrac{A_2}{A_1+A_2}L \end{cases} \quad \text{Equation 2}$$

the coordinates of the intercept point I(x$_1$, y$_1$, z$_1$) are determined by $$\begin{cases} x_i = x_1 + \dfrac{A_2}{A_1+A_2}(x_2-x_1) \\ y_i = y_1 + \dfrac{A_2}{A_1+A_2}(y_2-y_1) \\ z_i = z_1 + \dfrac{A_2}{A_1+A_2}(z_2-z_1) \end{cases} \quad \text{Equation 3}$$

or $$\begin{cases} x_i = x_2 - \dfrac{A_1}{A_1+A_2}(x_1-x_2) \\ y_i = y_2 + \dfrac{A_1}{A_1+A_2}(y_1-y_2) \\ z_i = z_2 + \dfrac{A_1}{A_1+A_2}(z_1-z_2) \end{cases} \quad \text{Equation 4}$$

Therefore the equation of the perpendicular plane P$_{12}$(x, y, z) is defined by $$(x_2-x_1)(x-x_i)+(y_2-y_1)(y-y_i)+(z_2-z_1)(z-z_i)=0 \quad \text{Equation 5}$$

where x$_i$, y$_i$, and z$_i$ can be found in Equation 3 or Equation 4.

The next step in the vector analysis is to determine the VA origin or exit site based on the initial phase vector matrix. As was shown above, any pair of unipolar recording sites can be used to define a vector therebetween and a plane perpendicular to this vector. Multiple perpendicular planes can be found when multiple pairs of unipolar recordings are available, as illustrated in the graph 600 of FIG. 6. The intersection of these planes may be used to find a candidate point for the VA origin or exit site.

Figure 6:
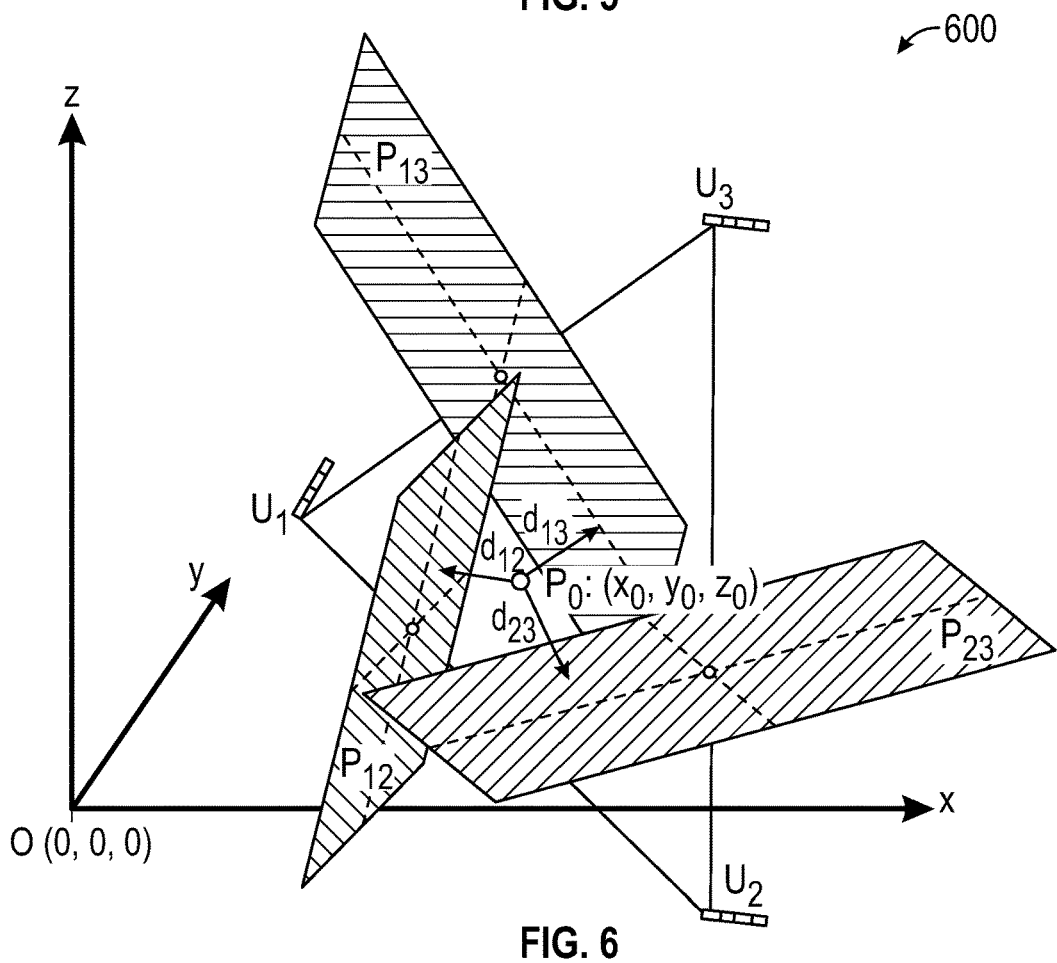
FIG. 6 is an example graph illustrating three vectors between three unipolar recording sites, three planes perpendicular to the three vectors, and an example candidate for an arrhythmia origin or exit site, in accordance with certain aspects of the present disclosure.

The graph 600 of FIG. 6 includes three unipolar recordings U$_1$, U$_2$, and U$_3$; three vectors U$_1$U$_2$, U$_2$U$_3$, and U$_1$U$_3$; and their associated perpendicular planes P$_{12}$, P$_{23}$, and P$_{13}$, respectively. According to analytical geometry, the distance of a point p$_0$: (x$_0$, y$_0$, z$_0$) to a plane P: Ax+By+Cz+D=0 can be calculated as $$d = \dfrac{Ax_0+By_0+Cz_0+D}{\sqrt{A^2+B^2+C^2}} \quad \text{Equation 6}$$

Figure 7:
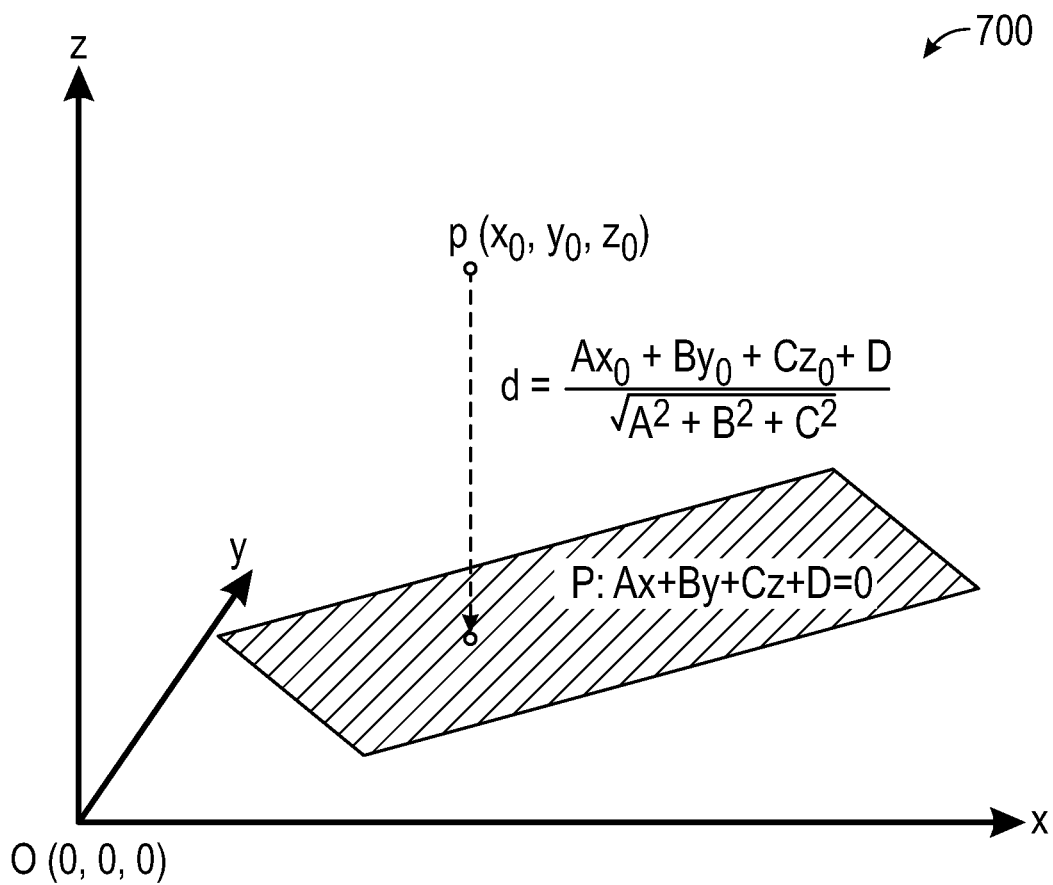
FIG. 7 is a graph illustrating determination of the distance between a point and a plane.

This concept is illustrated in the graph 700 of FIG. 7.

According to Equation 5, the equations of the three perpendicular planes in FIG. 6 can be each obtained and simplified as $$P_{12}: A_{12}x+B_{12}y+C_{12}z+D_{12}=0$$

$$P_{23}: A_{23}x+B_{23}y+C_{23}z+D_{23}=0$$

$$P_{13}: A_{13}x+B_{13}y+C_{13}z+D_{13}=0 \quad \text{Equation 7}$$

Inside the area surrounded by the three perpendicular planes in FIG. 6, the total distance of any given point p$_0$: (x$_0$, y$_0$, z$_0$) to each of the three perpendicular planes defined by Equation 7 can be calculated, according to Equation 6, as Equation 8 below.

$$d_{total} = \frac{A_{12}x_0 + B_{12}y_0 + C_{12}z_0 + D_{12}}{\sqrt{A_{12}^2 + B_{12}^2 + C_{12}^2}} + \\ \frac{A_{23}x_0 + B_{23}y_0 + C_{23}z_0 + D_{23}}{\sqrt{A_{23}^2 + B_{23}^2 + C_{23}^2}} + \\ \frac{A_{13}X_0 + B_{13}y_0 + C_{13}z_0 + D_{13}}{\sqrt{A_{13}^2 + B_{13}^2 + C_{13}^2}}$$

Equation 8

As long as these perpendicular planes are not parallel to each other, there exists a single point, referred to as the geometric median, whose total distance to each of the perpendicular planes is minimal. Existing algorithms, such as the Weiszfeld Algorithm, can be used to define the geometric median. When more than 3 (e.g., N) unipolar recordings are available, the total distance of a point to all the perpendicular planes can be calculated by Equation 9.

$$d_{total} = \sum_i^N \frac{A_i x_0 + B_i y_0 + C_i z_0 + D_i}{\sqrt{A_i^2 + B_i^2 + C_i^2}}$$

Equation 9

Thus, the geometric median may be determined by finding a point whose total distance to each of the perpendicular planes is minimal, such as with the above-mentioned Weiszfeld Algorithm. The coordinates of the geometric median may be considered as the candidate coordinates for the VA origin or exit site.

Note that vector and statistical analysis performed in this manner may lead to an estimated or calculated VA site that is located in space (e.g., located in a ventricular cavity), rather than in the heart tissue. In this case, the presumptive origin or exit site of the VA ($VAsite_0$) may be defined as the point on the heart tissue that is closest to the estimated or calculated VA site as determined by the vector and statistical analysis.

From a geometrical perspective, the heart 120 is a 3-D feature. While the vector analysis may be performed in 3-D using 3-D coordinates as described above, the 3-D heart (or a portion thereof, such as the ventricles) and the recording electrode sites may be projected to a 2-D plane (analogous to the 3-D globe of the Earth projected onto a 2-D world map). The vector analysis may then be conducted in the 2-D plane, and the candidate coordinates may then be back-projected into 3-D space to localize the VA origin or exit site, although such forward and back-projections may result in less precise localization of the VA origin or exit site.

Figure 8:
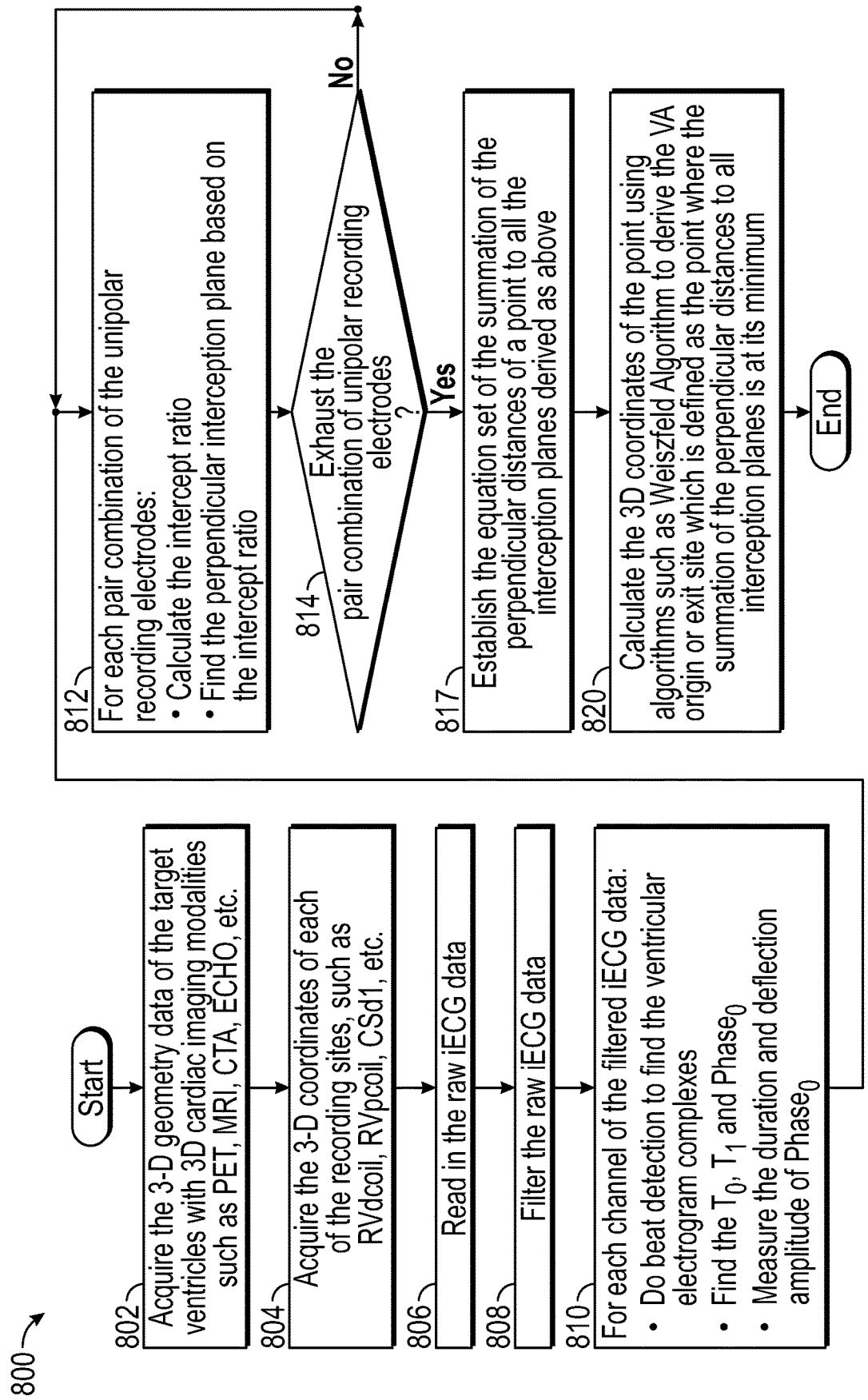
FIG. 8 is a flow diagram of example operations for using vector analysis to localize an arrhythmia origin or exit site, in accordance with certain aspects of the present disclosure.

FIG. 8 is a flow diagram of example operations 800 for using vector analysis to localize a VA origin or exit site, in accordance with certain aspects of the present disclosure. The operations 800 may be performed, for example, by the implantable device that stored the internal ECG signals, by another implantable device, by an external device that received the recorded internal ECG signals, or by a combination thereof.

The operations 800 may begin, at block 802, by acquiring the geometry data of the ventricles. Block 802 may be accomplished using any of various suitable imaging modalities, such as MRI, CTA, PET, echocardiography, etc.

At block 804, the coordinates of the electrodes (e.g., RVdcoil, RVpcoil, CSd1, etc.) that recorded the internal ECG signals are determined. This determination of the coordinates may be performed as described above and may involve an imaging system. For certain aspects, a lookup table (LUT) may be created with these coordinates.

At block 806, the internal ECG (iECG) signal data may be read. For example, the memory 154 may be read by the processor 152 to extract the internal ECG signal data. For certain aspects, this data may be processed and wirelessly communicated by transceiver 168 to another implantable device and/or to an external device (e.g., an ICD programmer). At optional block 808, the internal ECG signal data may be filtered (e.g., to remove noise and/or other unwanted signal content, such as high-frequency transients).

At block 810, multiple processes may be performed for each channel of the internal ECG signal data (e.g., for each unipolar recording). For example, beat detection may be performed on the channel to identify the ventricular electrogram complex. From the ventricular electrogram complex, $T_0$, $T_1$, and $Phase_0$ for each channel may be determined, as well as the duration D and amplitude A of the internal ECG signal during $Phase_0$ per channel, as described above.

At block 812, for each electrode-pair combination of the unipolar recording sites, the intercept ratio (e.g., L1:L2) may be calculated to determine an intercept point (e.g., $I(x_i, y_i, z_i)$) along the vector, and the perpendicular plane intercepting the vector at the intercept point may be determined. Once perpendicular planes have been found for all the electrode-pair combinations of the vector matrix, as ascertained at block 814, the operations 800 proceed to block 816.

At block 817, the equation set of the summation of the perpendicular distances of a point to the perpendicular planes is established (e.g., Equation 9).

At block 820, the coordinates of the point with the minimal summation distance are determined (e.g., using the Weiszfeld Algorithm). The resulting point (or the nearest point of actual heart tissue nearest this point with the minimal summation distance) is considered as the localized VA origin or exit site.

For certain aspects performed in 2-D, the coordinates of the localized VA origin or exit site may be back-projected from the 2-D plane to the 3-D geometry for the ventricles.

Example Conduction Time Analysis

Conduction time analysis is another type of quantitative analysis that may be performed to localize an arrhythmia origin or exit site based on internal ECG signals previously recorded during an arrhythmia event. Although this particular example conduction time analysis is explained below with respect to localizing a ventricular arrhythmia (VA) origin or exit site, those of ordinary skill in the art will understand that this technique may also be applied to localizing an atrial arrhythmia site.

This conduction time analysis may begin by determining a conduction time index (CTI) matrix based on intrinsic myocardial tissue characteristics of the individual subject's ventricles and their 3-D distributions. These tissue characteristics may include, but are not limited to, the scar content, the extent of ischemia, and/or the degree of myocardial edema.

Figure 9:
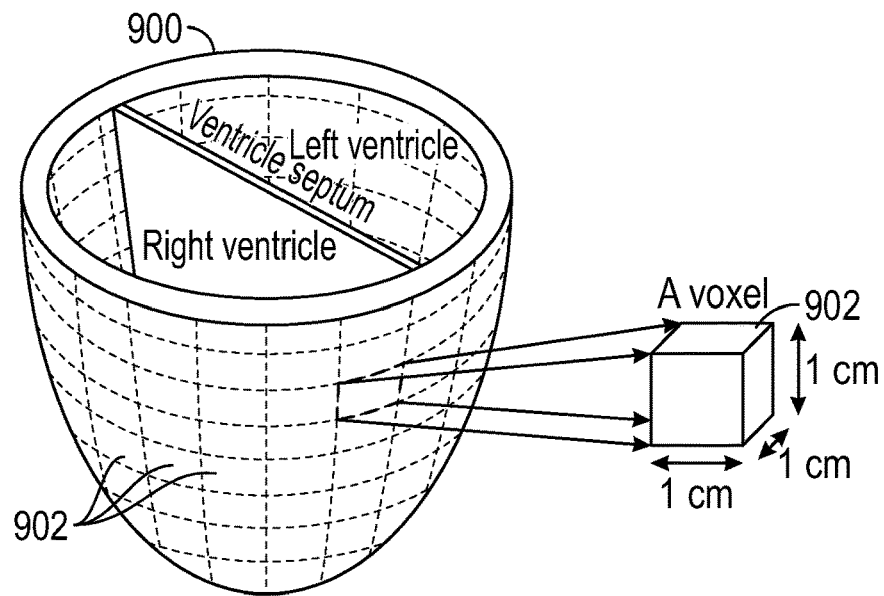
FIG. 9 illustrates a 3-D ellipsoid representing the ventricles of the heart divided into voxels and an example voxel, in accordance with certain aspects of the present disclosure.

The ventricles may be viewed as being composed of basic anatomic and functional units (volume elements, referred to as "voxels") of myocardial tissue, which are sufficiently small in volume so that the tissue characteristics within a given voxel may reasonably be considered as being uniform. Although one can define voxels of any size, it may be reasonable to set the voxel size to be 1.0×1.0×1.0 cm, as a non-limiting example. The actual dimensions of the voxel may depend on the spatial resolutions of the imaging modalities employed. Smaller voxel sizes may be used with better spatial resolutions, which may be more desirable for certain applications. Also, the dimensions of the voxel need not be equal on all sides (e.g., as in the case of a cuboid). FIG. 9 illustrates a 3-D ellipsoid 900 representing the ventricles of the heart 120 divided into voxels 902 and an example voxel, in accordance with certain aspects of the present disclosure.

As used herein, Scar Content (SC) generally refers to the volume percentage of scar in a given voxel 902 derived from cardiac imaging modalities. Suitable cardiac imaging modalities may include, but are not limited to, MRI T1 weighted images with and/or without enhancement using contrast agents such as gadolinium, a PET scan using isotopes such as fluorodeoxyglucose (FDG), and nuclear scan techniques using isotopes such as thallium with a viability protocol to define scarred region(s) in the heart. Each voxel 902 for an individual subject may be characterized with an SC provided by the imaging modality performed on the subject. As used herein, Ischemic Score (IS) generally refers to the quantification of ischemia determined by severity of ischemia and the volume percentage of the ischemia in a given voxel 902, where the severity of the ischemia is typically normalized to the myocardium with intact blood supply (typically identified as the region with the highest counts of isotopes) as derived from cardiac imaging modalities. Suitable cardiac imaging modalities for determining IS include, but are not limited to, a PET scan with isotope agents such as $^{82}$Rb or a nuclear scan with isotope agents such as thallium. Each voxel 902 for an individual subject may additionally or alternatively be characterized with an IS provided by the imaging modality performed on the subject. Likewise, the degree of edema in the ventricular myocardium may be determined by cardiac imaging modalities that include, but are not limited to MRI T2 weighted mapping. Each voxel 902 for an individual subject may additionally or alternatively be characterized with a degree of edema provided by the imaging modality performed on the subject. These indices (SC, IS, and degree of edema) are non-limiting examples of parameters of tissue characteristics that may be employed in the quantitative analysis of internal ECG signals based on their effects on conduction properties of individual voxels.

To calculate the conduction time index (CTI) matrix, the CTI of a given voxel 902 may be defined by tissue characteristics of the ventricles and derived from the values of SC and IS obtained from cardiac scans as described above. The CTI may be calculated according to an empirical equation, of which Equation 10 below is a non-limiting example:

$$CTI = \frac{EE}{(1-SC)*(1-IS)} \quad \text{Equation 10}$$

where EE (effect of edema) is a coefficient that reflects the negative effect of edema on myocardial conduction, which can be derived from analysis of regression models relating the degree of myocardial edema of each voxel, as quantified by cardiac imaging techniques such as MRI T2 weighted mapping, to intraventricular conduction during pacing maneuvers. EE will be a non-zero positive real number because there is always some degree of water content in any living myocardial tissue. In Equation 10, CTI will be highest if the myocardium represented by the voxel 902 is composed totally of fibrosis or scar tissue, which indicates conduction block at that site of the voxel. CTI will be lowest if the myocardium represented by the voxel 902 is completely healthy without any fibrotic or scar content, with normal blood supply and without edema (i.e., both SC and IS are essentially zero, and EE is minimal).

The reader is to understand that Equation 10 is only an example equation for calculating CTI; other equations based on the same or different tissue characteristics may alternatively be used. For example, a polynomial equation may be used to determine the CTI for each voxel, based on statistically determined polynomial coefficients.

Figure 10:
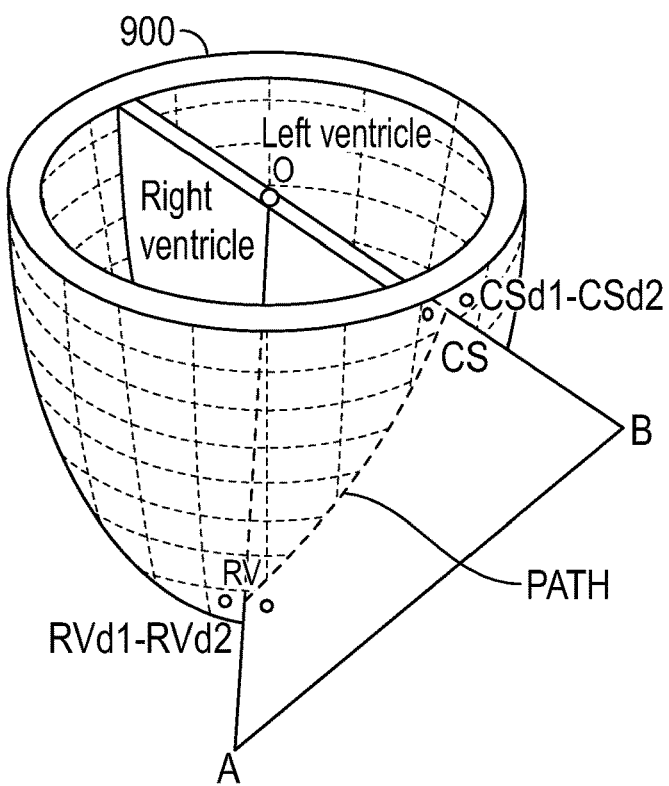
FIG. 10 illustrates the fastest conduction pathway (PATH) between two example pairs of near-field bipolar electrodes through the voxels of FIG. 9, as determined by a conduction time index (CTI) for each voxel, in accordance with certain aspects of the present disclosure.

Once the CTI matrix has been determined for the voxels 902, the fastest conduction pathway (PATH) between two pairs of near-field bipolar electrodes is determined, where the fastest conduction pathway is defined as the path through the voxels connecting the two pairs of near-field bipolar electrodes with the minimum sum of CTIs ($\Sigma$CTI). The locations of the bipolar electrodes and the voxels 902 may be registered based on the coordinate system described above. For example, FIG. 10 illustrates a first pair of near-field bipolar electrodes CSd1-CSd2 and a second pair of near-field bipolar electrodes RVd1-RVd2. A PATH is defined between the two pairs of electrodes based on the CTIs. In this example, the fastest conduction pathway (PATH) is also the shortest path (here, an arc) in terms of distance through the voxels 902 between the two pairs of electrodes, but this may not be the case. For example, the shortest distance between two pairs of electrodes may include a voxel 902 with a very high CTI, indicating slow conduction or even a conduction block. Therefore, the fastest conduction pathway may travel around this voxel or bypass several voxels in this region. The PATH will have a particular distance (DIS) through the underlying myocardium between the two pairs of near-field bipolar electrodes. A PATH and a DIS associated therewith may be determined for each different combination of two pairs of near-field bipolar electrodes based on the minimum $\Sigma$CTI between these two pairs of electrodes.

The conduction time analysis also involves determining a paced conduction time (PCT) between each different combination of two pairs of near-field bipolar electrodes. The PCT for each combination of two pairs of electrodes is defined as the time for a paced activation wave front from one near-field bipolar electrode pair to reach the other near-field bipolar electrode pair (supposedly along the PATH therebetween). The PCTs may be determined by using the ICD or other implantable device to introduce an electrical pacing stimulation into the heart 120 of the subject via one of the near-field bipolar electrode pairs (e.g., one of the electrode pairs in FIG. 1A, such as electrode pair 130) and to measure the local activation time (LAT) recorded on another near-field bipolar electrode pair (e.g., distal pair of electrodes on coronary sinus or LV lead, such as electrode pair 134) which represents the PCT from the pacing site (e.g., electrode pair 130) to the recording site (e.g., electrode pair 134). LAT is anatomically defined at the mid-point location between the recording pair of near-field bipolar electrodes. Once the PCT is determined, the average conduction velocity (ACV) along the PATH that is defined by DIS may be calculated, as shown in Equation 11 below:

$$ACV = \frac{DIS}{PCT} \quad \text{Equation 11}$$

The ACV may be calculated for each combination of two pairs of electrodes.

The conduction analysis may then proceed by determining a voxel conduction time (VCT) matrix. The VCT for a given voxel indexed by i along the PATH is estimated by the CTI of the voxel divided by the sum of all CTIs along the PATH and multiplied by the PCT for the PATH, as shown in Equation 12 below:

$$VCT_i = \frac{CTI_i}{\sum_i CTI_i} * \frac{DIS}{ACV} = \frac{CTI_i}{\sum_i CTI_i} * PCT \qquad \text{Equation 12}$$

The sum of the VCTs of all voxels 902 along the PATH equals the PCT for the PATH. VCT at a given voxel represents the estimated conduction time for the activation wave front to transverse the voxel. For certain aspects, a lookup table (LUT) for VCT may be established correlating the values of CTI to the values of VCT along the PATHs. Alternatively, one or more regression curves or models may be established relating CTI to VCT along the PATHs. The values of VCT at voxels that are not along the PATHs may be determined by the values of the respective CTI in reference to the LUT or by the regression curve(s). The complete set of VCTs (e.g., for all the voxels 902) will be the VCT matrix.

The VCT matrix forms the basis to draw 3-D isochrone contour lines in the myocardium that are centered at the midpoint between each pair of the near-field bipolar recording electrodes. Isochrone contour lines for a given near-field bipolar electrode pair connect surrounding voxels where the activation wave front, initiated by an electrical pacing stimulation delivered via this near-field bipolar electrode pair, concurrently arrives at the voxels (or at least within the same time range), hence the term "isochrone." For certain aspects, the isochrone contour lines may be constructed at temporally uniform increments (e.g., 5 ms or 10 ms increments) or at particular, selected time values of the activation wave front.

Figure 11:
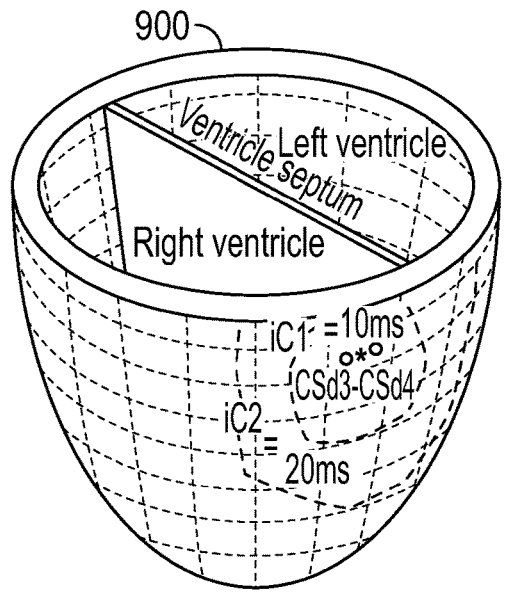
FIG. 11 illustrates example isochrone contour lines for a single pair of near-field bipolar recording electrodes drawn on the 3-D ellipsoid of FIG. 9, in accordance with certain aspects of the present disclosure.

FIG. 11 illustrates example isochrone contour lines iC1 and iC2 for a single pair of near-field bipolar recording electrodes (CSd3-CSd4) drawn on the 3-D ellipsoid 900. Although two isochrone contour lines are illustrated in FIG. 11, each pair of near-field bipolar recording electrodes may be associated with more than two isochrone contour lines. Please note the isochrone contour lines are, more precisely speaking, centered around the midpoint (as marked by the star in FIG. 11) between the near-field bipolar electrode pair (here, CSd3 and CSd4). Isochrone contour line iC1 represents the contour line along the voxels 902 where the propagation time of the activation wave front from the electrode pair to the voxels uniformly equals 10 ms (or in a range 10 ms±5 ms, for example). Isochrone contour line iC2 similarly represents the contour line where the wave front propagation time equals 20 ms (or in a range 20 ms±5 ms, for example). The non-limiting example increment of 10 ms between isochrone contour lines used in this illustration may be fixed or variable. Furthermore, the increment between isochrone contour lines may be constant, linearly varying, or nonlinearly varying.

The isochrone contour lines may be symmetric if the propagation condition is homogeneous. Under conditions of scar tissue, ischemic tissue, etc., there is usually no symmetry in the contour lines. For a given region of ventricular myocardium, the closer the isochrone lines lie together, the slower is the propagation of the activation wave front, or the lower the conduction velocity.

As described above, the VA initiation time ($T_0$) is defined as the earliest time at which unipolar and far-field bipolar internal ECG signals from any of the electrodes reveal a deflection, which may be either positive or negative. As used herein, the local activation time (VA-LAT) of a near-field bipolar electrode pair during VA is defined as the time interval from $T_0$ to the time when the myocardium underneath an individual near-field bipolar electrode pair is activated. The methodology for determining local activation times is well-known to those skilled in the art.

Figure 12:
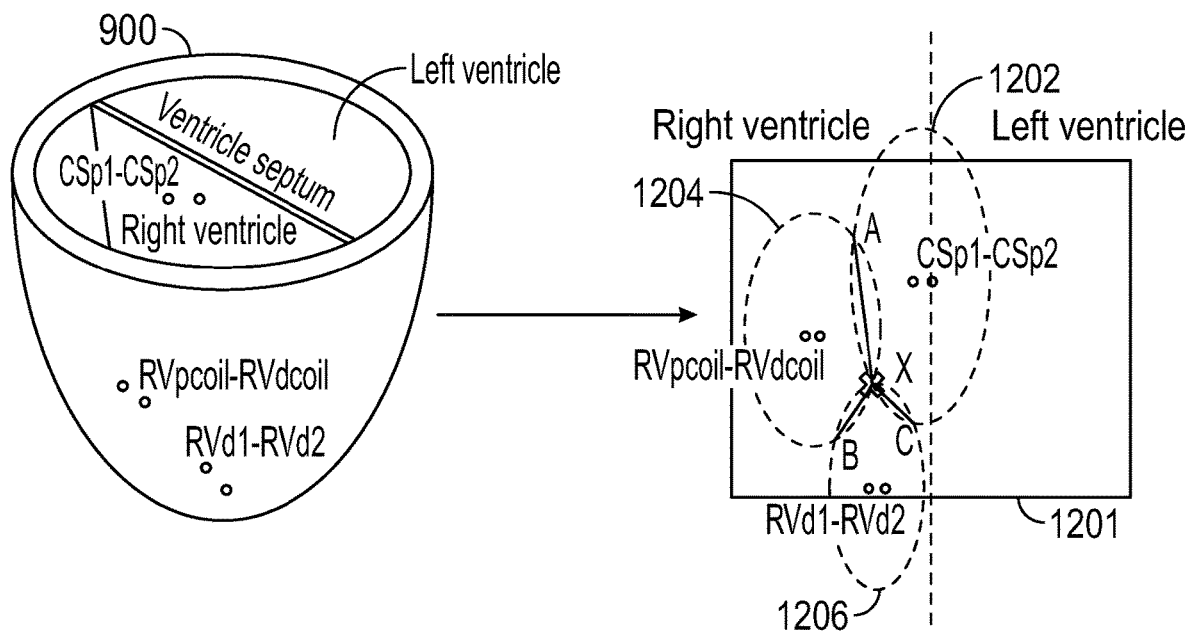
FIG. 12 illustrates the interception of multiple example isochrone contour lines for multiple near-field bipolar electrode pairs to localize a ventricular arrhythmia (VA) origin or exit site, in accordance with certain aspects of the present disclosure.

The presumptive origin or exit site of the VA ($VAsite_0$) may then be determined as the site where all isochrone contour lines, based on the values of the VA-LAT for a given near-field bipolar electrode pair, meet or intercept. This is demonstrated in FIG. 12. For simplicity of illustration and ease of understanding the concept, symmetric oval isochrone contour lines 1202, 1204, 1206 are projected onto a 2-D plane 1201 in FIG. 12, divided into right and left ventricles (RV and LV), although the isochrone contour lines in the 3-D ellipsoid 900 may be used instead (i.e., the determination of the intersection points may be performed in 3-D space rather than in a 2-D plane). In FIG. 12, the isochrone contour line 1202 of CSp1-CSp2 and the isochrone contour line 1204 of RVpcoil-RVdcoil intersect at points A and X. Likewise, the isochrone contour line 1204 of RVpcoil-RVdcoil and the isochrone contour line 1206 of RVd1-RVd2 intercept at points B and X, while the isochrone contour line 1202 of CSp1-CSp2 and the isochrone contour line 1206 of RVd1-RVd2 intercept at points C and X. The shared intercept point X among the isochrone contour lines 1202, 1204, 1206 is the candidate of VA origin or exit site.

Typically, however, all three isochrone contour lines do not share a single, common interception point. In this case, the point with the minimum sum of distances to the isochrone contour lines, may be identified as the VA origin or exit site as described below.

Once the coordinates of the final VA origin or exit candidate site (e.g., point X) in the 2-D plane 1201 are determined, the VA site (VA origin or exit) may be found by back-projecting the 2-D coordinates of point X to the 3-D ellipsoid 900 representing the ventricles. In other cases, the coordinates of the final VA site may be determined in 3-D space to begin with.

Figure 13:
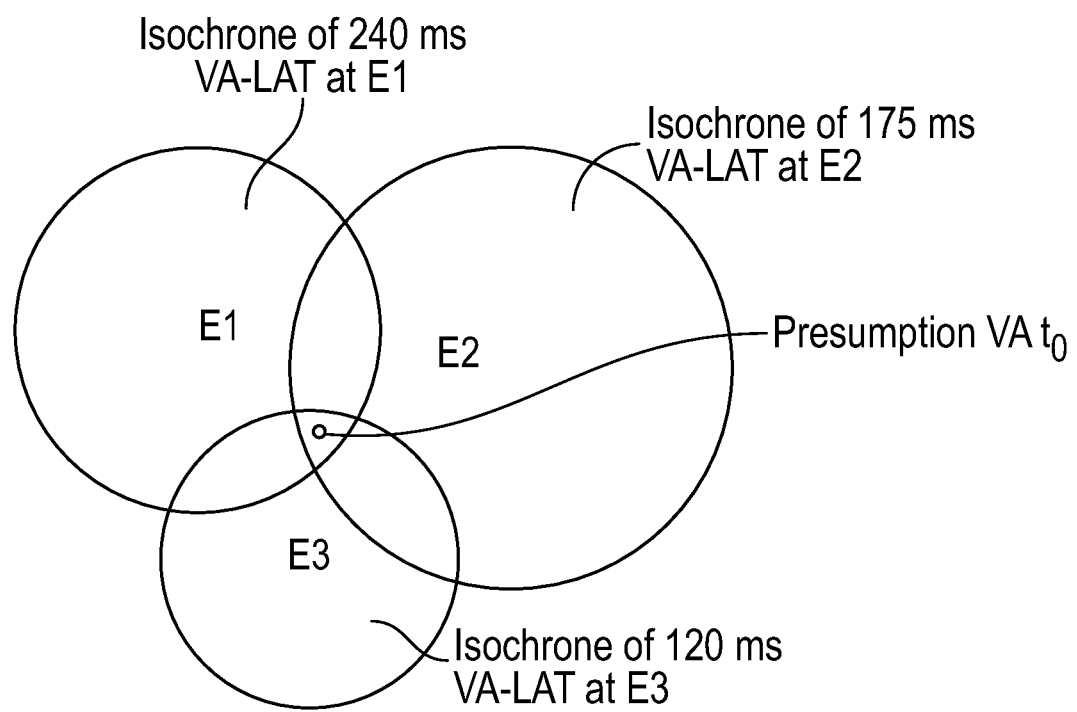
FIG. 13 illustrates the overlap of multiple example isochrone contour lines for multiple near-field bipolar electrode pairs to localize a VA origin or exit site, in accordance with aspects of the present disclosure.

FIG. 13 illustrates the overlap of three example isochrone contour lines for near-field bipolar electrode pairs represented by E1, E2, and E3, in accordance with aspects of the present disclosure. In the example of FIG. 13, electrode pair E1 has an isochrone contour line of 240 ms VA-LAT, electrode pair E2 has an isochrone contour line of 175 ms VA-LAT, and electrode pair E3 has an isochrone contour line of 120 ms VA-LAT. In this case, all three isochrone contour lines do not intersect, at a single point, as is the case for FIG. 12. Instead, the localization of the VA origin or exit site may be considered as a point within an area overlapped by all three isochrone contour lines, as illustrated in FIG. 13. For instance, this candidate point may be taken from the center of the overlapped area or from a point with the minimum sum of distances to the isochrone contour lines.

Figure 14:
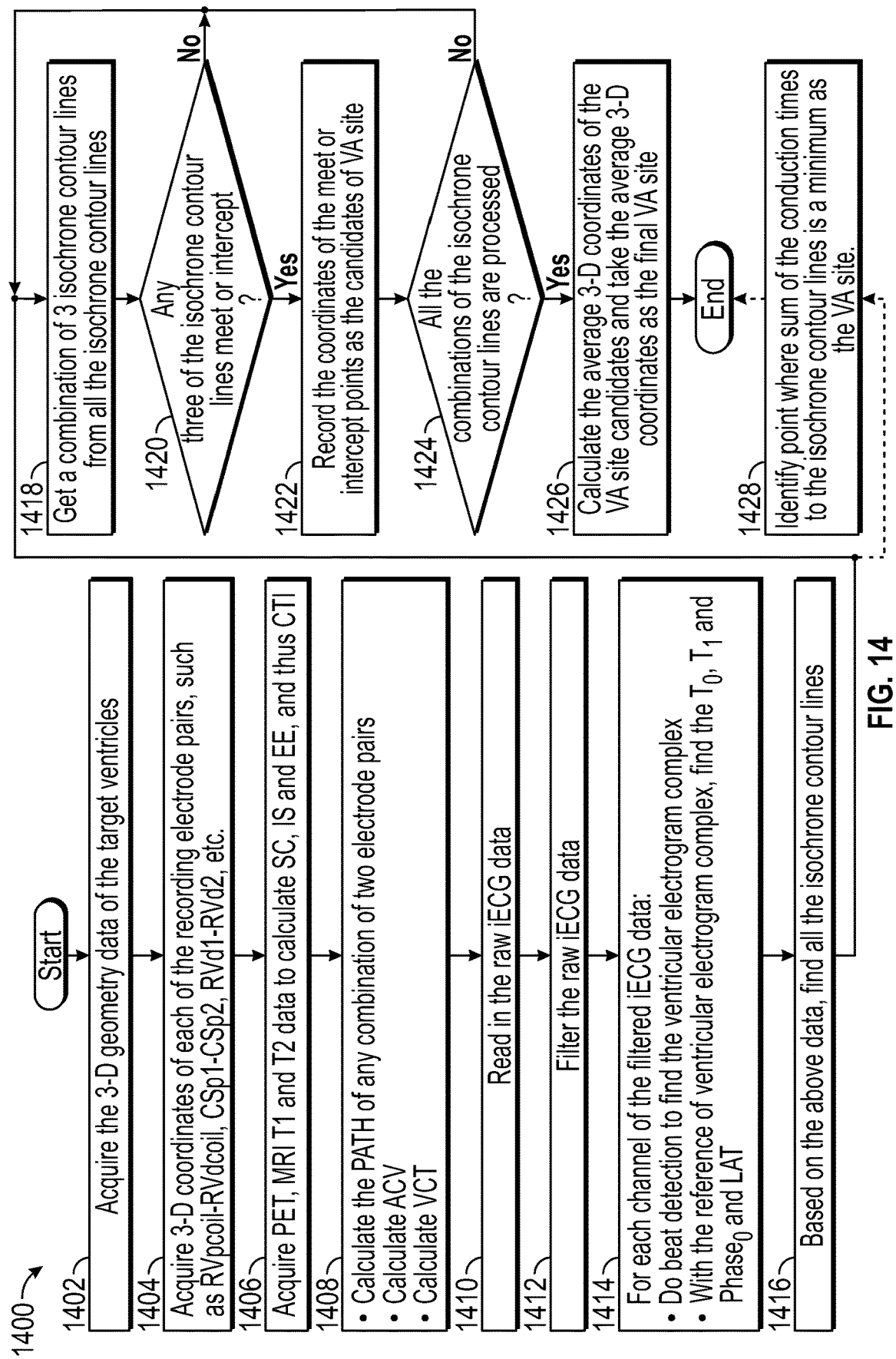
FIG. 14 is a flow diagram of example operations for using conduction time analysis to localize an arrhythmia origin or exit site, in accordance with certain aspects of the present disclosure.

FIG. 14 is a flow diagram of example operations 1400 for using conduction time analysis to localize a VA origin or exit site, in accordance with certain aspects of the present disclosure. The operations 1400 may be performed, for example, by the implantable device that stored the internal ECG signals, by another implantable device, by an external device that received the recorded internal ECG signals, or by a combination thereof.

The operations 1400 may begin, at block 1402, by acquiring 3-D geometry data of the ventricles (e.g., the ellipsoid 900). If the conduction time analysis is performed in 2-D, then the acquired 3-D geometry data may be mapped to a 2-D plane, for further analysis in 2-D.

At block 1404, the coordinates of the near-field bipolar electrode pairs (e.g., RVpcoil-RVdcoil, CSp1-CSp2, RVd1-RVd2, etc.) that recorded the internal ECG signals are determined. This determination of the coordinates may be performed as described above and may involve an imaging system. For certain aspects, a table may be created with these coordinates.

At block 1406, the intrinsic tissue characteristics (e.g., SC, IS, and/or EE) of the individual subject's ventricles may be determined, using any of various suitable techniques (e.g., PET, MRI T1, and/or MRI T2) as described above. These tissue characteristics may be assigned to corresponding voxels (e.g., voxels 902) in the 3-D geometry, and the CTI for each voxel may be calculated. At block 1408, the PATHs may be determined based on the CTIs. Then, the ACVs for each PATH may be calculated, and the VCTs for the voxels may be determined, as described above.

At block 1410, the internal ECG (iECG) signal data may be read. For example, the memory 154 may be read by the processor 152 to extract the internal ECG signal data. For certain aspects, this data may be processed and wirelessly communicated by transceiver 168 to another implantable device and/or to an external device (e.g., an ICD programmer). At optional block 1412, the internal ECG signal data may be filtered (e.g., to remove noise and/or other unwanted signal content, such as high-frequency transients).

At block 1414, multiple processes may be performed for each channel of the (filtered) internal ECG signal data (e.g., for each near-field bipolar recording). For example, beat detection may be performed on the channel to find the ventricular electrogram complex(es). From the ventricular electrogram complex, $T_0$, $T_1$, and $Phase_0$ for each channel may be determined, as well as the VA-LAT for each channel, as described above.

At block 1416, the isochrone contour lines for each near-field bipolar electrode pair may be determined, as described above. At block 1418, a combination of three isochrone contour lines are analyzed to determine if the three contour lines intersect at a single point. If not as determined at block 1420, then another combination of three isochrone contour lines are analyzed at block 1418. If so as determined at block 1420, then the coordinates of the intersection point are recorded as a candidate for the VA origin or exit site at block 1422. If all possible combinations of isochrone contour lines have not yet been analyzed as determined at block 1424, the operations 1400 return to block 1418 for analysis of another combination of three isochrone contour lines. If all combinations of isochrone contour lines have been analyzed as determined at block 1424, the operations 1400 proceed to block 1426.

At block 1426, a statistical analysis may be performed on the coordinates of the candidates for the VA origin or exit site. For example, the coordinates may be averaged, a weighted average of the coordinates may be calculated, or a least-squares error analysis based on the coordinates and/or isochrone contour lines may be performed. The resulting coordinates from the statistical analysis are considered as the location of the presumptive VA origin or exit site ($VAsite_0$).

As an alternative to the operations described in block 1418 to block 1426, the presumptive VA origin or exit site may be derived, at optional block 1428, by identifying the point in the ventricular myocardium where the sum of the conduction times, calculated based on the VCT matrix, from this point to all the isochrone contour lines (determined at block 1416) is at a minimum. The coordinates of this point coordinates are considered as the location of the presumptive VA origin or exit site ($VAsite_0$).

If the operations 1400 were performed in 2-D, the coordinates of the localized VA origin or exit site may be back-projected from the 2-D plane to the 3-D geometry for the ventricles. However, such forward and back-projections between 3-D and 2-D space may result in less precise localization of the VA origin or exit site.

Example Intraoperative Refinement of Arrhythmia Localization

The quantitative analysis of the internal ECG data ($iECG_0$) recorded during a VA event results in the identification of a presumptive VA origin or exit ($VAsite_0$). However, because of the simplified nature of the quantitative analyses described above and the complexity and individual variations of anatomy and underlying pathophysiology of the mammalian heart, $VAsite_0$ may be further refined during or just before an ablation procedure to improve the anatomic accuracy in determining the VA origin or exit as the final target for ablation energy application. Although the intraoperative refinement technique is explained below with respect to localizing a VA origin or exit site, those of ordinary skill in the art will understand that this technique may also be applied to localizing an atrial arrhythmia site.

For certain aspects, vector analysis may be used for this intraoperative refinement. In this case, pacing with a roving pacing or ablation catheter at the $VAsite_0$ will generate a new set of internal ECG data ($iECG_1$). Subtracting $iECG_0$ (the initial iECG data recorded during VA) from $iECG_1$ yields $\Delta iECG_1$. From $\Delta iECG_1$, a new vector matrix ($Vector_1$) during $Phase_0$ may be derived, where $Phase_0$ is defined above. The starting point of $Vector_1$ will be $VAsite_0$ with a magnitude and direction determined by $Vector_1$. The end point of $Vector_1$ will be the updated presumptive VA origin ($VAsite_1$), which may be likewise pinned to the nearest ventricular myocardial surface.

Next, the same roving catheter or a separate pacing catheter may be moved to $VAsite_1$, and the procedure described above may be repeated for an $n^{th}$ time, where n is a positive integer, until (1) the magnitude of the vector derived from $\Delta iECG_n$ is below a predetermined threshold (e.g., within a tolerance of error, such as 2.5 or 0.5 mm); (2) the morphologies of all unipolar and far-field bipolar internal ECG signals during pacing, $iECG_n$, match their counterparts recorded during VA with a correlation coefficient above a particular percentage (e.g., 90%, 95%, or higher); or (3) the minimal value of $Vector_n$ is reached. The final value of minimal $Vector_n$ may be an indicator for endocardial, intramural, or epicardial location of the VA. The final updated site of VA ($VAsite_{final}$) at the completion of this procedure may be considered as the site of origin (for focal VAs) or the exit site (for reentrant VAs).

For other aspects, conduction time analysis may be used for the intraoperative refinement procedure. In this case, the set of local activation times at all the near-field bipolar electrode pairs during VA forms a VA-LAT matrix. Pacing with a roving pacing or ablation catheter at the $VAsite_0$ will generate a new set of local activation times or $P-LAT_1$ at all the near-field bipolar electrode pairs (iECG$_1$) with the time of pacing stimulus. Subtracting VA-LAT from P-LAT$_1$ yields ΔLAT$_i$ which may be treated mathematically as a "time" vector (T-vector$_1$) and be translated into a displacement vector (D-vector$_1$) which starts at VAsite$_0$ and ends at the updated presumptive VA origin VAsite$_1$. The D-vector$_1$'s direction will be identical to that of T-vector$_1$ and its magnitude, which will be determined by the magnitude of T-vector$_1$ in time and the VCTs of individual voxels along the same direction such that the summation of these CVTs equals the magnitude of T-vector$_1$.

Next, the same roving catheter or a separate pacing catheter will be moved to VAsite$_1$, and the procedure described above may be repeated for an n$^{th}$ time, where n is a positive integer, until (1) the magnitude of the D-vector$_n$ derived from T-vector$_n$ is below a predetermined threshold (e.g., within a tolerance of error, such as 2.5 or 0.5 mm); (2) the morphologies of all unipolar and far-field bipolar iECG signals during pacing, iECG$_n$, match their counterparts recorded during VA with a correlation coefficient above a particular percentage (e.g., 90%, 95%, or higher); or (3) the minimal value of D-vector$_n$ is reached. The final value of minimal D-vector$_n$ may be an indicator for endocardial, intramural, or epicardial location of the VA. The final updated site of VA (VAsite$_{final}$) will be considered as the site of origin (for focal VAs) or the exit site (for reentrant VAs).

The quantitative analysis techniques described herein are meant to be illustrative of how a device could utilize the information contained in the stored internal ECG data and are not meant to be exclusive. Other methods may be used, such as internal ECG morphology matching alone or in combination with surface lead ECG morphology, if available. Furthermore, the quantitative analyses as described herein and other quantitative analysis techniques may be performed by themselves or in combination (e.g., the results thereof may be combined to localize the VA origin or exit site). For instance, conduction time analysis may be employed to identify the initial presumptive VA site (VAsite$_0$), and then vector analysis may be employed intraoperatively to fine tune the localization of the VA origin or exit site, as described above. Likewise, this sequence of techniques may be altered or reversed.

Example Computer-Readable Medium and System for Analyzing a VA

Certain aspects of the present disclosure provide a non-transitory computer-readable medium having instructions stored thereon that, when executed by at least one processor, cause the processor to perform operations for analyzing an arrhythmia in a subject. The operations (e.g., operations 200) generally include reading, from an implantable device implanted in the subject, a plurality of internal electrocardiograph (ECG) signals sensed and stored by the implantable device while the subject was experiencing an arrhythmia event; performing an analysis of the read internal ECG signals; and determining a localization of the arrhythmia based on the analysis.

According to certain aspects, the implantable device has multiple leads with a plurality of electrodes for sensing the internal ECG signals.

According to certain aspects, there is a delay between a time when the internal ECG signals were stored and a time of the reading. For example, the delay may be in a range from a few minutes to a few days to a few weeks.

According to certain aspects, the determined localization has a resolution of at most 2.0 cm, 1.0 cm, or 0.5 cm.

According to certain aspects, performing the analysis comprises performing a vector analysis of the internal ECG signals. For certain aspects, performing the analysis further entails determining physical locations of a plurality of electrodes implanted in the subject, associated with the implantable device, and used to sense the internal ECG signals. In this case, the processor may perform the vector analysis based on the determined physical locations of the plurality of electrodes. For certain aspects, the determined physical locations of the electrodes are based on computed tomography (CT), magnetic resonance imaging (MRI), echocardiography, or positron emission tomography (PET), performed on the subject.

According to certain aspects, performing the analysis comprises performing a conduction time analysis of the internal ECG signals. For certain aspects, performing the analysis further entails determining physical locations of a plurality of electrodes implanted in the subject, associated with the implantable device, and used to sense the internal ECG signals. In this case, the processor may perform the conduction time analysis based on the determined physical locations of the plurality of electrodes. For certain aspects, the determined physical locations of the electrodes are based on computed tomography (CT), magnetic resonance imaging (MRI), echocardiography, or positron emission tomography (PET), performed on the subject.

According to certain aspects, the operations further involve receiving one or more (myocardial) tissue characteristics of the heart of the subject. In this case, performing the analysis may entail performing the analysis of the read internal ECG signals and the received tissue characteristics.

According to certain aspects, the subject is a human patient. For other aspects, the subject may be a pig or a dog, for example.

According to certain aspects, the operations further include reading, from the implantable device, derivatives of the sensed internal ECG signals stored by the implantable device. For certain aspects, at least one of the sensed internal ECG signals or the derivatives thereof is stored in a digital format. For other aspects, at least one of the sensed internal ECG signals or the derivatives thereof are stored in an analog format.

According to certain aspects, the implantable device is capable of administering an electric shock to a heart of the subject.

According to certain aspects, the implantable device comprises an implantable cardioverter/defibrillator (ICD). For other aspects, the implantable device comprises a pacemaker.

Certain aspects provide a system for analyzing an arrhythmia in a subject. The system generally includes a wireless communications device and at least one processor communicatively coupled to the wireless communications device. The wireless communications device is configured to read, from an implantable device implanted in the subject, a plurality of internal ECG signals sensed and stored by the implantable device while the subject was experiencing an arrhythmia event. The at least one processor is configured to perform an analysis of the read internal ECG signals and to determine a localization of the arrhythmia based on the analysis.

According to certain aspects, the subject is a human patient. For other aspects, the subject may be a pig or a dog, for example.

According to certain aspects, the implantable device has multiple leads with a plurality of electrodes for sensing the internal ECG signals.

According to certain aspects, there is a delay between a time when the internal ECG signals were stored and a time of the reading. For example, the delay is in a range from a few minutes to a few days (or to a few weeks).

According to certain aspects, the determined localization has a resolution of at most 2.0 cm, at most 1.0 cm, or at most 0.5 cm.

According to certain aspects, the processor is configured to perform the analysis by performing a vector analysis of the internal ECG signals. For certain aspects, the processor is further configured to perform the analysis by determining physical locations of a plurality of electrodes implanted in the subject, associated with the implantable device, and used to sense the internal ECG signals. In this case, the processor is configured to perform the vector analysis based on the determined physical locations of the plurality of electrodes. For certain aspects, determining the physical locations of the electrodes entails performing CT, MRI, echocardiography, or PET, on the subject.

According to certain aspects, the processor is configured to perform the analysis by performing a conduction time analysis of the internal ECG signals. For certain aspects, the processor is further configured to perform the analysis by determining physical locations of a plurality of electrodes implanted in the subject, associated with the implantable device, and used to sense the internal ECG signals. In this case, the processor is configured to perform the conduction time analysis based on the determined physical locations of the plurality of electrodes. For certain aspects, determining the physical locations of the electrodes entails performing CT, MRI, echocardiography, or PET, on the subject.

According to certain aspects, the processor is further configured to receive one or more (myocardial) tissue characteristics of the heart of the subject. In this case, the processor may be configured to perform the analysis by performing the analysis of the read internal ECG signals and the received tissue characteristics.

According to certain aspects, the implantable device is capable of administering an electric shock to a heart of the subject.

According to certain aspects, the implantable device comprises an ICD. For other aspects, the implantable device comprises a pacemaker.

According to certain aspects, the wireless communications device is further configured to read, from the implantable device, derivatives of the sensed internal ECG signals stored by the implantable device. The sensed internal ECG signals or the derivatives thereof may be stored in a digital format, in an analog format, or in some combination thereof.

Certain aspects of the present disclosure provide an implantable device for implanting in a subject. The implantable device generally includes multiple leads with a plurality of electrodes for sensing a plurality of internal ECG signals; and a memory configured to store the sensed internal ECG signals at least while the subject is experiencing an arrhythmia and to subsequently read out the stored internal ECG signals for analysis to determine a localization of the arrhythmia.

According to certain aspects, the implantable device further includes a transmitter configured to transmit the stored internal ECG signals to an external device for analysis to determine the localization of the arrhythmia.

According to certain aspects, the implantable device further includes a processor configured to analyze the stored internal ECG signals read from the memory to determine the localization of the arrhythmia.

According to certain aspects, the implantable device further includes a capacitive element configured to administer an electric shock to a heart of the subject via at least a portion of the leads.

According to certain aspects, the implantable device comprises an ICD. For other aspects, the implantable device comprises a pacemaker.

According to certain aspects, the implantable device includes at least two leads with at least four electrodes. For example, the implantable device may include at least two leads with at least two electrodes on each of the at least two leads According to certain aspects, the plurality of electrodes are configured for placement for the determination of the localization of the arrhythmia within a chamber of a heart of the subject with a spatial resolution (e.g., <2.0 cm, such as 0.5 cm) sufficient to guide an ablation catheter to the determined localization for ablation therapy.

According to certain aspects, the memory is further configured to store derivatives of the sensed internal ECG signals and to read out the derivatives. The sensed internal ECG signals or the derivatives thereof may be stored in a digital and/or analog format.

Any of the operations described above, such as the operations 200, 800, and 1400, may be included as instructions in a computer-readable medium for execution by a processing system. The (non-transitory) computer-readable medium may comprise any suitable memory or other storage device for storing instructions, such as read-only memory (ROM), random access memory (RAM), flash memory (e.g., USB flash drive), an electrically erasable programmable ROM (EEPROM), a compact disc ROM (CD-ROM), a floppy disk, or a digital versatile disc ROM (DVD-ROM).

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

As used herein (including the claims that follow), a phrase referring to "at least one of" a list of items refers to any combination of those items, including single members. As an example, "at least one of: x, y, and z" is intended to cover: x, y, z, x-y, x-z, y-z, x-y-z, and any combination thereof (e.g., x-y-y and x-x-y-z).

While the foregoing is directed to certain aspects of the present disclosure, other and further aspects may be devised without departing from the basic scope thereof, and the scope thereof is determined by the claims that follow.

What is claimed is:

1. A method of analyzing an arrhythmia in a subject, comprising:
    reading a first plurality of internal electrocardiograph (ECG) signals sensed and recorded while the subject was experiencing an arrhythmia event;
    performing an analysis of the first plurality of internal ECG signals; and
    determining a localization of the arrhythmia based on the analysis,
    wherein the analysis includes:
        for each voxel in a plurality of voxels in a myocardial tissue:
            determining a conduction time index based on at least one tissue characteristic of a portion of the myocardial tissue associated with the voxel;

determining a conduction path based at least in part on the conduction time index; and based on at least one paced conduction, deriving a voxel conduction time across the voxel for the conduction time index along the conduction path;

generating at least one 3D isochrone contour line based at least in part on the voxel conduction time of each voxel in the plurality of voxels; and determining the localization of arrhythmia based at least in part on the at least one 3D isochrone contour line.

2. The method of claim 1, further comprising:

assisting guidance of a catheter inserted into the subject to the determined localization of the arrhythmia; and performing ablation of heart tissue of the subject at the localization using the catheter.

3. The method of claim 2, further comprising:

delivering, via a roving catheter, electrical pacing stimulations at multiple sites in one or more chambers of a heart of the subject;

sensing and recording a second plurality of internal ECG signals during the delivery of the electrical pacing stimulations;

analyzing differences between the second plurality of internal ECG signals and the first plurality of internal ECG signals; and refining the localization of the arrhythmia based on the analysis, wherein the ablation is performed on the refined localization of the arrhythmia.

4. The method of claim 1, wherein the at least one tissue characteristic of the portion of the myocardial tissue comprises at least one of a scar content, an ischemic score, or a degree of myocardial edema.

5. The method of claim 1, wherein the analysis further includes performing a vector analysis of the first plurality of internal ECG signals.

6. The method of claim 1, further comprising:

determining physical locations of a plurality of electrodes implanted in the subject to sense the first plurality of internal ECG signals, wherein the physical locations of the plurality of electrodes are determined in reference to a region of a heart of the subject; and performing the analysis of the first plurality of internal ECG signals based on the determined physical locations of the plurality of electrodes.

7. The method of claim 6, wherein determining the physical locations of the electrodes comprises performing at least one of fluoroscopy, computed tomography (CT), magnetic resonance imaging (MRI), echocardiography, or positron emission tomography (PET), on the subject.

8. The method of claim 1, further comprising:

reading a second plurality of internal ECG signals sensed and recorded while the subject was experiencing another arrhythmia event;

performing an analysis of the second plurality of internal ECG signals;

determining a localization of another arrhythmia based on the analysis of the second plurality of internal ECG signals; and comparing the localization of the arrhythmia and the localization of the other arrhythmia to determine whether the localizations comprise a same site in a heart of the subject.

9. The method of claim 1, wherein reading the first plurality of internal ECG signals comprises reading from an implantable device and wherein the implantable device has multiple leads with a plurality of electrodes for sensing the first plurality of internal ECG signals.

10. The method of claim 1, wherein determining the localization of arrhythmia comprises identifying the at least one 3D isochrone contour line that matches a local activation time recorded from an internal electrode during the arrhythmia.

11. A system for analyzing an arrhythmia in a subject, comprising:

a communications device configured to read a first plurality of internal electrocardiograph (ECG) signals sensed and recorded while the subject was experiencing an arrhythmia event; and at least one processor communicatively coupled to the communications device and configured to:

perform an analysis of the first plurality of internal ECG signals;

and determine a localization of the arrhythmia based on the analysis, wherein performing the analysis by the at least one processor includes the at least one processor further configured to:

for each voxel in a plurality of voxels in a myocardial tissue:

determine a conduction time index based on at least one tissue characteristic of a portion of the myocardial tissue associated with the voxel;

determine a conduction path based at least in part on the conduction time index; and based on at least one paced conduction, derive a voxel conduction time across the voxel for the conduction time index along the conduction path;

generate at least one 3D isochrone contour line based at least in part on the voxel conduction time of each voxel in the plurality of voxels; and determine the localization of arrhythmia based at least in part on the at least one 3D isochrone contour line.

12. The system of claim 11, wherein the at least one processor is further configured to perform a vector analysis of the first plurality of internal ECG signals.

13. The system of claim 11, wherein the at least one processor is further configured to:

determine physical locations of a plurality of electrodes implanted in the subject to sense the first plurality of internal ECG signals, wherein the physical locations of the plurality of electrodes are determined in reference to a region of a heart of the subject; and perform the analysis of the plurality of internal ECG signals based on the determined physical locations of the plurality of electrodes.

14. A non-transitory computer-readable medium having instructions stored thereon that, when executed by at least one processor, cause the at least one processor to perform operations for analyzing an arrhythmia in a subject, the operations comprising:

reading a plurality of internal electrocardiograph (ECG) signals sensed and recorded while the subject was experiencing an arrhythmia event;

performing an analysis of the plurality of internal ECG signals;

and determining a localization of the arrhythmia based on the analysis, wherein the operations to perform the analysis includes further operations comprising:

for each voxel in a plurality of voxels in a myocardial tissue:

determining a conduction time index based on at least one tissue characteristic of a portion of the myocardial tissue associated with the voxel;

determining a conduction path based at least in part on the conduction time index; and based on at least one paced conduction, deriving a voxel conduction time across the voxel for the conduction time index along the conduction path;

generating at least one 3D isochrone contour line based at least in part on the voxel conduction time of each voxel in the plurality of voxels; and determining the localization of arrhythmia based at least in part on the at least one 3D isochrone contour line.

15. A method of determining a location of an arrhythmia in a subject, comprising:

reading a first plurality of electrocardiograph (ECG) signals from a device recorded during the arrhythmia;

performing a conduction time analysis of the first plurality of ECG signals, wherein the conduction time analysis includes generating a 3D isochrone contour line based on a conduction time across a portion of a myocardial tissue; and determining the location of the arrhythmia based on the conduction time analysis.

16. The method of claim 15, wherein the determining the location of the arrhythmia includes determining a conduction pathway based on the conduction time in at least the portion of the myocardial tissue.

17. The method of claim 15, wherein performing the conduction time analysis includes analyzing tissue characteristics of at least the portion of the myocardial tissue.

18. The method of claim 17, wherein the tissue characteristics comprise at least one of a scar content, an ischemic score, or a degree of myocardial edema.

19. The method of claim 15, further comprising:

sensing a second plurality of ECG signals during a delivery of at least one of electrical and pacing stimulations by a roving catheter;

analyzing differences between the second plurality of ECG signals sensed during the delivery of the at least one of electrical stimulations and pacing and the first plurality of ECG signals; and refining the location of the arrhythmia based on the analysis.

20. The method of claim 19, further comprising:

determining a conduction time difference based on the analyzed differences, wherein the conduction time difference comprises of a direction and a magnitude of refinement for the location of arrhythmia; and refining the location based on the direction and the magnitude of the conduction time difference.

21. The method of claim 20, wherein refining the location includes refining the location until the magnitude of the conduction time difference is lower than a predetermined threshold.

22. The method of claim 20, wherein refining the location includes refining the location until a morphology of the second plurality of ECG signals match a morphology of the first plurality of ECG signals.

23. The method of claim 20, wherein refining the location includes refining the location until the magnitude of the conduction time difference derived is of a minimal value.

* * * * *